United States Patent
Yoo et al.

(10) Patent No.: US 10,047,041 B2
(45) Date of Patent: Aug. 14, 2018

(54) AMINO-PHENYL-SULFONYL-ACETATE DERIVATIVES AND USE THEREOF

(71) Applicant: CJ Healthcare Corporation, Seoul (KR)

(72) Inventors: Jae Ho Yoo, Yongin-si (KR); Seung Chan Kim, Suwon-si (KR); Soo Yeon Jung, Seoul (KR); Hyoung Rok Bak, Seoul (KR); Young Mee Chung, Yongin-si (KR); Sung Jun Kim, Yongin-si (KR); Sook Kyung Park, Seoul (KR); Seog Beom Song, Suwon-si (KR); Shin-Young Ryu, Seoul (KR); Mi Young Yoon, Cheonan-si (KR); Dong Hyun Ko, Gwacheon-si (KR); Sun Young Park, Yongin-si (KR); Chi Hye Park, Seongnam-si (KR); Nak Hyun Choi, Yongin-si (KR)

(73) Assignee: CJ HEALTHCARE CORPORATION, Seoul (KR)

( * ) Notice: Subject to any disclaimer, the term of this patent is extended or adjusted under 35 U.S.C. 154(b) by 0 days.

(21) Appl. No.: 15/506,211

(22) PCT Filed: Jul. 14, 2015

(86) PCT No.: PCT/KR2015/007290
 § 371 (c)(1),
 (2) Date: Feb. 23, 2017

(87) PCT Pub. No.: WO2016/032120
 PCT Pub. Date: Mar. 3, 2016

(65) Prior Publication Data
 US 2017/0247320 A1 Aug. 31, 2017

(30) Foreign Application Priority Data

Aug. 27, 2014 (KR) .................. 10-2014-0112536
Jul. 3, 2015 (KR) .................. 10-2015-0095308

(51) Int. Cl.
 *C07C 317/14* (2006.01)
 *C07D 307/79* (2006.01)
 *C07D 307/52* (2006.01)
 *C07D 213/36* (2006.01)
 *C07D 317/46* (2006.01)
 *C07D 319/16* (2006.01)

(52) U.S. Cl.
 CPC .......... *C07C 317/14* (2013.01); *C07D 213/36* (2013.01); *C07D 307/52* (2013.01); *C07D 307/79* (2013.01); *C07D 317/46* (2013.01); *C07D 319/16* (2013.01)

(58) Field of Classification Search
 CPC .. C07C 317/14; C07D 317/46; C07D 307/52; C07D 213/36; C07D 319/16; C07D 307/79
 See application file for complete search history.

(56) References Cited

U.S. PATENT DOCUMENTS 7,750,048 B2   7/2010  Kuo et al.
7,960,369 B2   6/2011  Fukatsu et al.

FOREIGN PATENT DOCUMENTS

| JP | 2002-503717 A | 2/2002 | |
|----|----|----|----|
| KR | 10-2001-0041089 | 6/2007 | |
| WO | WO-9942436 A1 * | 8/1999 | ........... C07D 211/20 |
| WO | WO 2004/041266 A1 | 5/2004 | |
| WO | WO 2013/128378 A1 | 9/2013 | |

OTHER PUBLICATIONS

Ito, N., "A medium-term rat liver bioassay for rapid in vivo detection of carcinogenic potential of chemicals." Cancer science 94.1 (2003): 3-8. (Year: 2003).*
International Search Report in connection with PCT International Application No. PCT/KR2015/007290.
Anne-Marie Faucher, et al., "Discovery of Small-Molecule Inhibitors of the ATPase Activity of Human Papillomavirus E1 Helicase", J. Med. Chem, 2004, 47, 18-21.
Mar. 20, 2018 Japanese official action in connection with corresponding Japanese Patent Application No. 2017-511334.
Venkatesan Aranapakam et al., "Synthesis and Structure-Activity Relationship of N-Substituted 4-Arylsulfonylpiperidine-4-hydroxamic Acids as Novel, Orally Active Matrix Metalloproteinase Inhibitors for the Treatment of Osteoarthritis" J. Med. Chem., 2003, vol. 46, No. 12, p. 2376-2396.
Apr. 11, 2018 European search report in connection with corresponding European Patent Application No. 15835298.9.
Garrido D. M. et al., "Synthesis and activity of small molecule GPR40 agonists" Bioorganic & Medicinal Chemistry Letters, vol. 16, No. 7, Apr. 1, 2006 p. 1840-1845.

* cited by examiner

*Primary Examiner* — John M Mauro
(74) *Attorney, Agent, or Firm* — John P. White; Cooper & Dunham LLP

(57) ABSTRACT

The present invention relates to a novel amino-phenyl-sulfonyl-acetate derivative or a pharmaceutically acceptable salt thereof; and a pharmaceutical composition for preventing or treating diabetes comprising the same as an active ingredient.

22 Claims, 1 Drawing Sheet

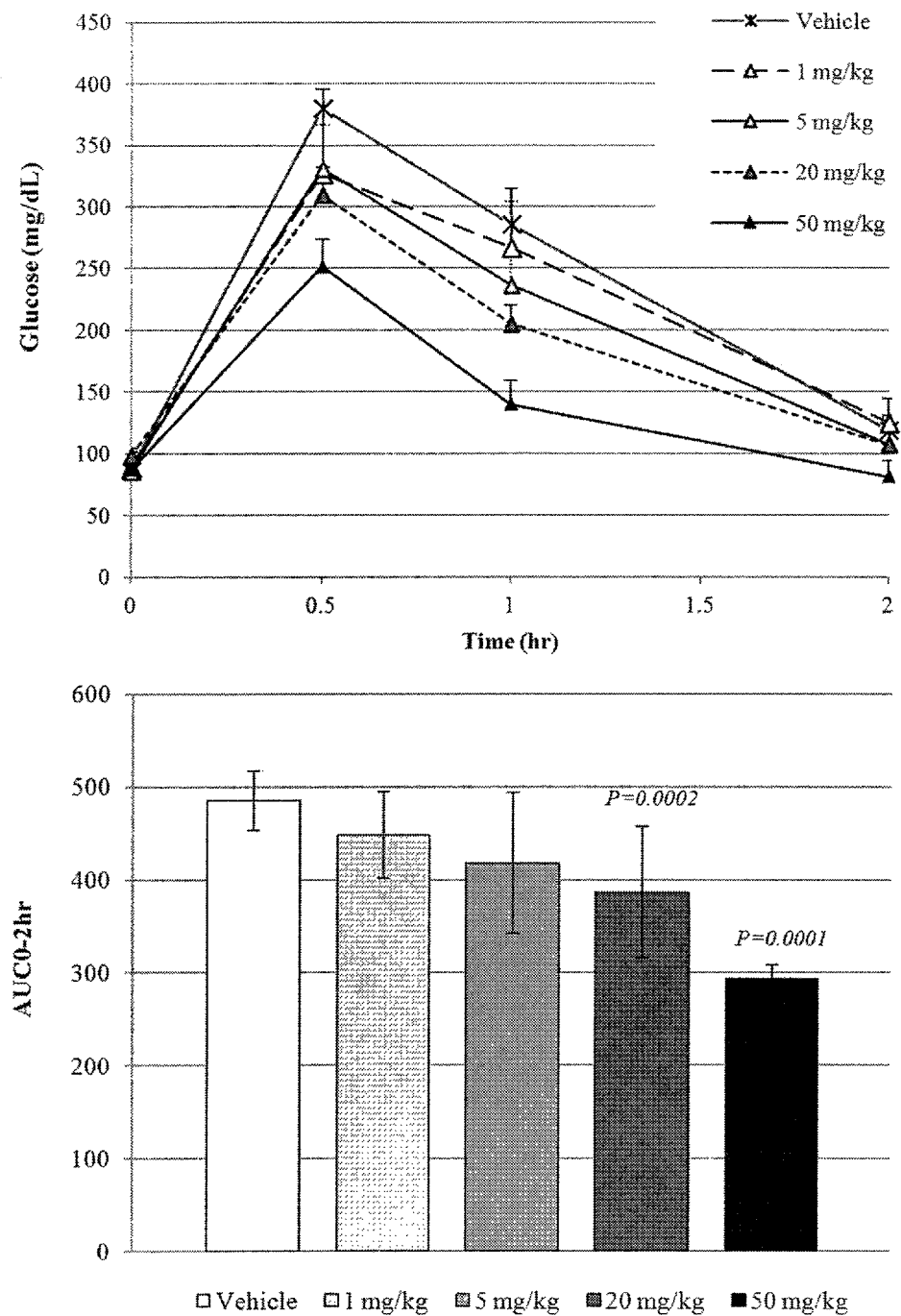

AMINO-PHENYL-SULFONYL-ACETATE DERIVATIVES AND USE THEREOF

CROSS-REFERENCE TO RELATED APPLICATIONS

This application is a § 371 national stage of PCT International Application No. PCT/KR2015/007290, filed Jul. 14, 2015, claiming priority of Korean Patent Applications Nos. KR 10-2015-0095308, filed Jul. 3, 2015 and KR 10-2014-0112536, filed Aug. 27, 2014 the content of each of which is hereby incorporated by reference into the application.

TECHNICAL FIELD

The present invention relates to novel amino-phenyl-sulfonyl-acetate derivatives or a pharmaceutically acceptable salt thereof; and a pharmaceutical composition for preventing or treating diabetes comprising the same as an active ingredient.

BACKGROUND ART

Type 2 insulin resistance diabetes is a typical metabolic disease which accounts for about 90% of the total diabetes cases. The main substance which controls blood glucose present in the body is insulin, and the insulin gets secreted through complex signaling pathways when insulin receptors receive a stimulus. In type 2 diabetes, insulin resistance may occur, in which organs such as muscle, liver, pancreas, etc. do not respond properly to insulin. Normally, when the concentration of blood glucose increases, the insulin secretion also increases to help the concentration of blood glucose return to a normal level, but insulin is not properly secreted in patients with type 2 diabetes, and thus, a high blood glucose level is maintained which may directly lead to diabetes.

The therapeutic agents currently used to treat type 2 diabetes include insulin, metformin, a substance which suppresses the glucose production by the liver, sulfonylureas, substances which stimulate insulin secretion from the beta cells in the pancreas, α-glucosidase inhibitor, a substance which inhibits glucose absorption, and thiazolidine derivatives, substances which enhance insulin sensitivity, etc., and recently, exenatide, which is a GLP-1 analog, DPP IV inhibitors, SGLT-2 inhibitors, which inhibit glucose absorption in the kidney, etc. are used. However, adverse side effects including hypoglycemia caused by insulin, gastrointestinal side effects caused by metformin, etc., edema by caused by thiazolidine derivatives, etc. have been reported, and in addition, pancreatitis caused by GLP-1 analogs and DPP IV inhibitors, and urinary tract infection caused by SGLT-2 have also been reported. Therefore, research has been actively conducted to develop novel therapeutic agents for diabetes which can effectively lower blood glucose without causing side effects.

DISCLOSURE

Technical Problem

The present inventors have made extensive efforts to find a novel compound which can serve as a therapeutic agent for diabetes, and as a result, they have confirmed that a series of amino-phenyl-sulfonyl-acetate derivatives can be effectively used to prevent or treat type 2 diabetes, thereby completing the present invention.

Technical Solution

One objective of the present invention is to provide novel amino-phenyl-sulfonyl-acetate derivatives or a pharmaceutically acceptable salt thereof.

Another objective of the present invention is to provide a pharmaceutical composition for preventing or treating diabetes comprising the compound or a pharmaceutically acceptable salt thereof as an active ingredient.

Advantageous Effect

The compound of novel amino-phenyl-sulfonyl-acetate derivatives of the present invention is effective in lowering blood glucose, and thus can be useful in the treatment of type 2 diabetes.

BRIEF DESCRIPTION OF DRAWING

The drawing shows the effect of lowering blood glucose according to the dose of the compound of Example 1 of the present invention.

BEST MODE FOR CARRYING OUT INVENTION

In a first aspect, the present invention provides a compound represented by Formula 1 below and a pharmaceutically acceptable salt thereof:

[Formula 1]

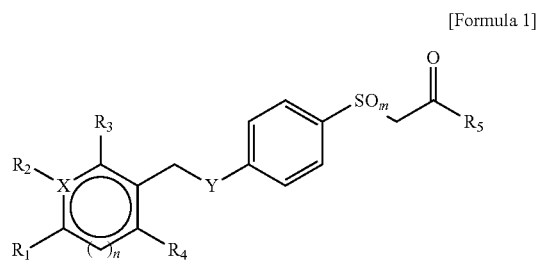

wherein,
X is C or O;
Y is NH or O;
m is an integer of 1 or 2;
n is an integer of 0 or 1;
$R_1$ is hydrogen, $C_{1-4}$ alkyl, or $C_{1-4}$ alkoxy; or forms a $C_{5-10}$ hydrocarbon ring connected with $R_2$;
$R_2$ is absent or hydrogen, halogen, aryloxy, or aryl or heteroaryl selected from the group consisting of phenyl, pyrazinyl, pyrazolyl, pyridinyl, pyrimidinyl, thiazolyl, and thienyl,
wherein the aryl or heteroaryl is unsubstituted, or independently substituted with at least one substituent selected from the group consisting of $C_{1-4}$ alkyl, $C_{1-4}$ alkoxy, $C_{1-4}$ haloalkyl, $C_{1-4}$ hydroxyalkyl, hydroxy, halogen, nitro, cyano, amino, $C_{1-4}$ alkyl-amino, acetyl-amino, formyl, —(C═O)—($C_{1-4}$ alkyl), —(C═O)-morpholino, —(C═O)—$NR_6R_7$, morpholino, piperazinyl, piperidinyl, $C_{1-4}$ alkyl-$SO_2$—$C_{1-4}$ alkoxy, —$SO_2$—($C_{1-4}$ alkyl), and —$SO_2$—$NR_6R_7$ directly or through a straight or branched $C_{1-4}$ alkyl chain, or forms an unsubstituted or halogen substituted 5- to 7-membered ring joined through two adjacent substituent groups, said ring comprising 0 to 2 oxygen atoms;

$R_3$ and $R_4$ are each independently hydrogen, halogen, $C_{1-4}$ alkyl, $C_{1-4}$ alkoxy, nitro, cyano, amino, $C_{1-4}$ alkyl-amino, acetyl-amino, formyl, —(C=O)—($C_{1-4}$ alkyl), —(C=O)-morpholino, —(C=O)—$NR_6R_7$, morpholino, piperazinyl, piperidinyl, —$SO_2$—($C_{1-4}$ alkyl), and —$SO_2$—$NR_6R_7$;

$R_5$ is hydroxy, $C_{1-4}$ alkoxy, or $C_{1-4}$ alkyl-aminooxy; and $R_6$ and $R_7$ are each independently hydrogen or $C_{1-4}$ alkyl.

Specifically, in the Formula above, $R_1$ may be hydrogen, methyl, or ethoxy. Or, it may form a $C_{5-10}$ hydrocarbon ring connected with $R_2$, but is not limited thereto.

Specifically, in the Formula above, $R_2$ may be absent; hydrogen; halogen; aryloxy; or phenyl or pyridinyl which is unsubstituted or independently substituted with 1 to 3 substituents selected from the group consisting of $C_{1-4}$ alkyl, $C_{1-4}$ alkoxy, $C_{1-4}$ haloalkyl, $C_{1-4}$ hydroxyalkyl, $C_{1-4}$ alkyl-$SO_2$—$C_{1-4}$ alkoxy, hydroxy, and halogen, or forms an unsubstituted or halogen-substituted 5- to 7-membered ring joined through two adjacent substituent groups, said ring comprising 0 to 2 oxygen atoms.

Specifically, in the Formula above, $R_2$ may be absent; hydrogen; bromo; phenyloxy; benzofuranyl; 2,3-dihydrobenzo[b][1,4]dioxynyl; or phenyl, pyridinyl, or benzo[d][1,3]dioxolyl unsubstituted or substituted with 1 to 3 substituents selected from the group consisting of methyl, ethyl, methoxy, ethoxy, trifluoromethyl, hydroxymethyl, methylsulfonyl-propoxy, hydroxy, fluoro, and chloro.

Specifically, in the Formula above, $R_3$ and $R_4$ may each independently be hydrogen, halogen, $C_{1-4}$ alkyl, $C_{1-4}$ alkoxy, nitro, cyano, or amino More specifically, $R_3$ and $R_4$ may each independently be hydrogen, fluoro, methyl, or methoxy.

Specifically, in the Formula above, $R_5$ may be hydroxyl, but is not limited thereto, or it may be $C_{1-4}$ alkoxy or $C_{1-4}$ alkyl-aminooxy which can be readily converted to a hydroxyl group via hydrolysis.

Specifically, in the Formula above, when X is C, Y may be NH or O; m may be an integer of 1 or 2; n may be an integer of 1; $R_1$ may be hydrogen, methyl, or ethoxy, or forms a tetrahydro-naphthalene ring connected with $R_2$; $R_2$ may be hydrogen; bromo; phenyloxy; benzofuranyl; 2,3-dihydrobenzo[b][1,4]dioxynyl; or phenyl, pyridinyl, or benzo[d][1,3]dioxolyl unsubstituted or substituted with 1 to 3 substituents selected from the group consisting of methyl, ethyl, methoxy, ethoxy, trifluoromethyl, hydroxymethyl, methyl-sulfonyl-propoxy, hydroxy, fluoro, and chloro; $R_3$ and $R_4$ may each independently be hydrogen, fluoro, methyl, or methoxy; and $R_5$ may be hydroxy.

Or in the Formula above, when X is O, Y may be NH; m may be an integer of 1 or 2; n may be an integer of 0; $R_1$ may be hydrogen; $R_2$ may be absent; $R_3$ and $R_4$ may be both hydrogen; and $R_5$ may be hydroxy.

More specifically, the compound may be:
1) 2-(4-((2'-methyl-biphenyl-3-yl)methylamino)phenylsulfonyl)acetic acid,
2) 2-(4-(3-(benzofuran-5-yl)benzylamino)phenylsulfonyl) acetic acid,
3) 2-(4-(3-phenoxybenzylamino)phenylsulfonyl)acetic acid,
4) 2-(4-(3-bromobenzylamino)phenylsulfonyl)acetic acid,
5) 2-(4-((2',6'-dimethyl-4'-(3-(methylsulfonyl)propoxy)biphenyl-3-yl)methylamino)phenylsulfonyl)acetic acid,
6) 2-(4-((2',6'-dimethylbiphenyl-3-yl)methylamino)phenylsulfonyl)acetic acid,
7) 2-(4-((4'-fluorobiphenyl-3-yl)methylamino)phenylsulfonyl)acetic acid,
8) 2-(4-((3'-methoxybiphenyl-3-yl)methylamino)phenylsulfonyl)acetic acid,
9) 2-(4-((4-fluoro-2'-methylbiphenyl-3-yl)methylamino) phenylsulfonyl)acetic acid,
10) 2-(4-((2',4-dimethylbiphenyl-3-yl)methylamino)phenylsulfonyl)acetic acid,
11) 2-(4-((4-methoxy-2'-methylbiphenyl-3-yl)methylamino)phenylsulfonyl)acetic acid,
12) 2-(4-((2-fluoro-2'-methylbiphenyl-3-yl)methylamino) phenylsulfonyl)acetic acid,
13) 2-(4-((2-methoxy-2'-methylbiphenyl-3-yl)methylamino)phenylsulfonyl)acetic acid,
14) 2-(4-((4-fluoro-2',3'-dimethylbiphenyl-3-yl)methylamino)phenylsulfonyl)acetic acid,
15) 2-(4-((4-fluoro-2',4'-dimethylbiphenyl-3-yl)methylamino)phenylsulfonyl)acetic acid,
16) 2-(4-((2-fluorobiphenyl-3-yl)methylamino)phenylsulfonyl)acetic acid,
17) 2-(4-((2-methoxybiphenyl-3-yl)methylamino)phenylsulfonyl)acetic acid,
18) 2-(4-((4-methoxy-2',3'-d methylbiphenyl-3-yl)methylamino)phenylsulfonyl)acetic acid,
19) 2-(4-(2-methoxybenzylamino)phenylsulfonyl)acetic acid,
20) 2-(4-(3-methoxybenzylamino)phenylsulfonyl)acetic acid,
21) 2-(4-(2-methylbenzylamino)phenylsulfonyl)acetic acid,
22) 2-(4-(4-ethoxybenzylamino)phenylsulfonyl)acetic acid,
23) 2-(4-(furan-3-yl-methylamino)phenylsulfonyl)acetic acid,
24) 2-(4-(3-(pyridin-3-yl)benzylamino)phenylsulfonyl)acetic acid,
25) 2-(4-(3-(pyridin-4-yl)benzylamino)phenylsulfonyl)acetic acid,
26) 2-(4-(3-(benzo[d][1,3]dioxol-5-yl)benzylamino)phenylsulfonyl)acetic acid,
27) 2-(4-(3-(2,2-difluoro-benzo[d][1,3]dioxol-5-yl)benzylamino)phenylsulfonyl)acetic acid,
28) 2-(4-(3-(4-fluoro-benzo[d][1,3]dioxol-5-yl)benzylamino)phenylsulfonyl)acetic acid,
29) 2-(4-(3-(2,3-dihydrobenzo[b][1,4]dioxin-6-yl)benzylamino)phenylsulfonyl)acetic acid,
30) 2-(4-(3-(2-methylpyridin-4-yl)benzylamino)phenylsulfonyl)acetic acid,
31) 2-(4-(3-(2-hydroxypyridin-4-yl)benzylamino)phenylsulfonyl)acetic acid,
32) 2-(4-(3-(2-methoxypyridin-4-yl)benzylamino)phenylsulfonyl)acetic acid,
33) 2-(4-(3-(2-ethoxypyridin-4-yl)benzylamino)phenylsulfonyl)acetic acid,
34) 2-(4-((4'-methylbiphenyl-3-yl)methylamino)phenylsulfonyl)acetic acid,
35) 2-(4-(biphenyl-3-yl-methylamino)phenylsulfonyl)acetic acid,
36) 2-(4-((3',4'-dimethylbiphenyl-3-yl)methylamino)phenylsulfonyl)acetic acid,
37) 2-(4-((2',4'-dimethylbiphenyl-3-yl)methylamino)phenylsulfonyl)acetic acid,
38) 2-(4-((2',3'-dimethylbiphenyl-3-yl)methylamino)phenylsulfonyl)acetic acid,
39) 2-(4-((2',5'-dimethylbiphenyl-3-yl)methylamino)phenylsulfonyl)acetic acid, 40) 2-(4-((4'-ethylbiphenyl-3-yl-methylamino)phenylsulfonyl)acetic acid,
41) 2-(4-((2'-ethylbiphenyl-3-yl)methylamino)phenylsulfonyl)acetic acid,
42) 2-(4-((3',5'-dimethylbiphenyl-3-yl)methylamino)phenylsulfonyl)acetic acid,
43) 2-(4-((4'-methoxy-2'-methylbiphenyl-3-yl)methylamino)phenylsulfonyl)acetic acid,
44) 2-(4-((4'-methoxy-2',6'-dimethylbiphenyl-3-yl)methylamino)phenylsulfonyl)acetic acid,
45) 2-(4-((3'-methylbiphenyl-3-yl)methylamino)phenylsulfonyl)acetic acid,
46) 2-(4-((3',4'-dimethoxybiphenyl-3-yl)methylamino)phenylsulfonyl)acetic acid,
47) 2-(4-((4'-chloro-2'-methylbiphenyl-3-yl)methylamino)phenylsulfonyl)acetic acid,
48) 2-(4-((4'-chloro-2'-(trifluoromethyl)biphenyl-3-yl)methylamino)phenylsulfonyl)acetic acid,
49) 2-(4-((2',4',6'-trimethylbiphenyl-3-yl)methylamino)phenylsulfonyl)acetic acid,
50) 2-(4-((2'-methoxybiphenyl-3-yl)methylamino)phenylsulfonyl)acetic acid,
51) 2-(4-((4'-fluoro-2'-methylbiphenyl-3-yl)methylamino)phenylsulfonyl)acetic acid,
52) 2-(4-((2'-(trifluoromethyl)biphenyl-3-yl)methylamino)phenylsulfonyl)acetic acid,
53) 2-(4-((5'-chloro-2'-methylbiphenyl-3-yl)methylamino)phenylsulfonyl)acetic acid,
54) 2-(4-((2',6'-dimethoxybiphenyl-3-yl)methylamino)phenylsulfonyl)acetic acid,
55) 2-(4-((2'-(hydroxymethyl)biphenyl-3-yl)methylamino)phenylsulfonyl)acetic acid,
56) 2-(4-((2',6'-dimethylbiphenyl-3-yl)methylamino)phenylsulfonyl)acetic acid,
57) 2-(4-((4-fluoro-2',6'-dimethylbiphenyl-3-yl)methylamino)phenylsulfonyl)acetic acid,
58) 2-(4-((2',6'-dimethylbiphenyl-3-yl)methoxy)phenylsulfonyl)acetic acid,
59) 2-(4-((2'-ethyl-6-methylbiphenyl-3-yl)methoxy)phenylsulfonyl)acetic acid,
60) 2-(4-((2'-methylbiphenyl-3-yl)methylamino)phenylsulfinyl)acetic acid,
61) 2-(4-((2',6'-dimethylbiphenyl-3-yl)methylamino)phenylsulfinyl)acetic acid,
62) 2-(4-((4-fluoro-2',6'-dimethylbiphenyl-3-yl)methylamino)phenylsulfinyl)acetic acid,
63) 2-(4-(3-phenoxybenzylamino)phenylsulfinyl)acetic acid, or
64) 2-(4-((9,10-dihydrophenanthrene-3-yl)methylamino)phenylsulfinyl)acetic acid.

The compound of the present invention may be present in the form of a pharmaceutically acceptable salt. An acid addition salt formed by a pharmaceutically acceptable free acid may be useful for the salt. As used herein, the term "pharmaceutically acceptable salt" of the present invention has a concentration which is relatively non-toxic and has innocuous adverse effects to patients and refers to any organic or inorganic acid addition salts of the compound which do not deteriorate the advantageous effects of the compound represented by Formula 1 caused by the salt.

The acid addition salt may be prepared by a conventional method, for example, by dissolving the compound in an excess amount of acid aqueous solution, followed by precipitation of the salt using a water-miscible organic solvent, for example, methanol, ethanol, acetone, or acetonitrile. The same molar amount of the compound and acid or alcohol in water (for example, glycol monomethyl ether) may be heated, and subsequently, the compound can be dried by evaporation, or the extracted salt may be collected by suction filtration.

In addition, a pharmaceutically acceptable metal salt may be prepared using a base. An alkali metal salt or alkali earth metal salt may be obtained, for example, by dissolving the compound in an alkali metal hydroxide or alkali earth metal hydroxide solution, and filtering non-soluble salt of the compound, followed by evaporating and drying the filtrate.

In addition, the present invention includes not only the compound represented by Formula 1 above and a pharmaceutically acceptable salt thereof, but also solvates which can be prepared therefrom.

Further, if the compound of the present invention has an asymmetric carbon center in the substituents thereof, it may exist as R or S isomers, racemates, diastereomeric mixtures, and individual diastereomers, and all of the isomers and the mixture thereof are included in the scope of the present invention.

For example, the compound of the present invention can be synthesized from nitrobenzenethiol through a series of reactions represented by Reaction 1. However, Reaction 1 is provided for illustrative purposes only, and the preparation method of the compound of the present invention should not be limited thereto in any manner, and it may be carried out by a method known in the art, or by various modifications.

[Reaction 1]

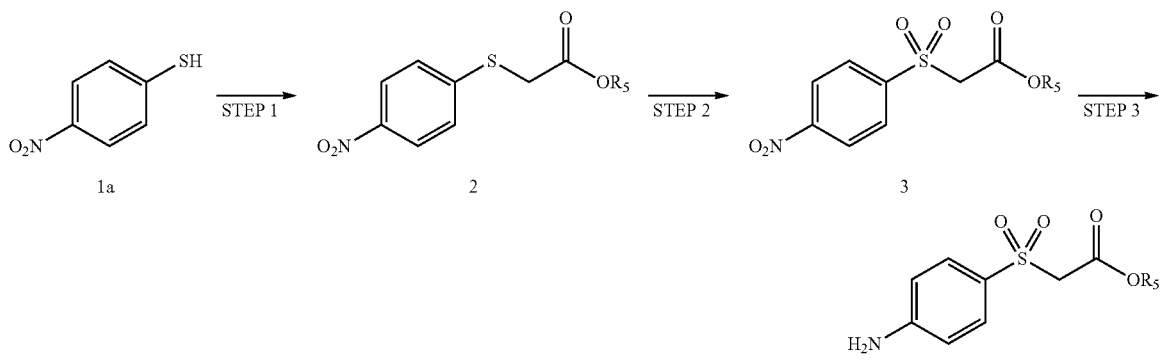

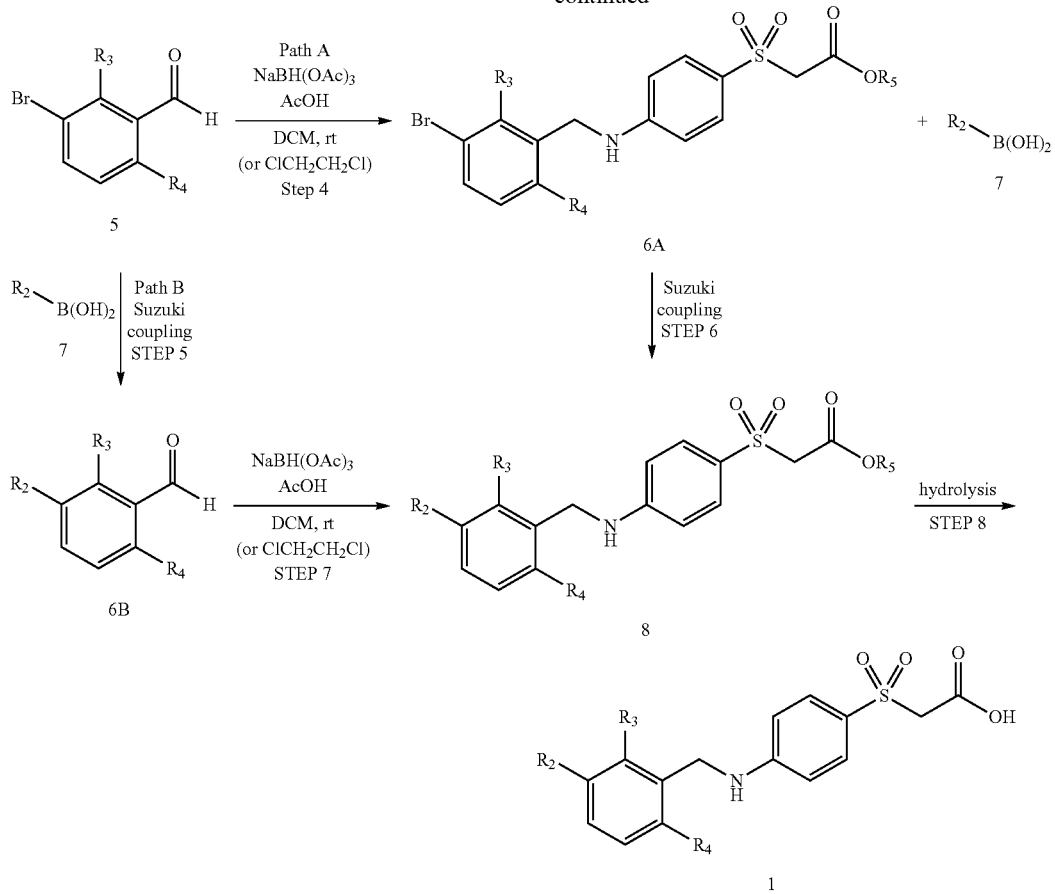

In the Reaction above, the substituents are as previously defined.

Specifically, 4-nitrobenzenethiol, which is a compound represented as 1a, is reacted with bromoacetate to synthesize the compound of Formula 2 (STEP1), and the compound of Formula 2 is oxidized and converted into a sulfone compound (STEP2), and subsequently, a nitrile group is reduced to obtain the compound of Formula 4.

A 2-(4-aminophenyl sulfonyl) acetate derivative (or acetic acid), which is represented by Formula 4 obtained via the series of reactions mentioned above, is reacted with a halo benzaldehyde derivative including a reactive halogen group represented by Formula 5 at a position where a substituent is to be introduced to prepare the compound represented by Formula 6A (STEP 4). Preferably, sodium triacetoxyborohydride and dichloromethane ($CH_2Cl_2$) may be used as a reducing reagent and a solvent, respectively, but are not limited thereto.

Then, the compound of Formula 6A is reacted with a boronic acid derivative including a substituent to be introduced thereto via the Suzuki reaction to obtain the compound represented by Formula 8 (STEP 6) (Path A).

Meanwhile, the compound represented by Formula 8 may also be obtained when the two reactions are carried out in a reverse direction (Path B). Specifically, the reaction of the halo benzaldehyde derivative of Formula 5 and the boronic acid derivative may be carried out via the Suzuki reaction to introduce a substituent (STEP 5), and then the product thereof may be reacted with the 2-(4-aminophenyl sulfonyl) acetate derivative (or acetic acid) represented by Formula 4 to synthesize the compound of Formula 8 (STEP 7).

Lastly, if necessary, the thus-obtained compound of Formula 8 may be hydrolyzed to remove the substituent, and the final target compound may be obtained in the form of an acetic acid derivative. The hydrolysis may be preferably carried out in the presence of LiOH, KOH, or NaOH, and as a solvent, tetrahydrofuran, methanol, water, or, a mixture thereof may be used, but the hydrolysis and solvent are not limited thereto.

In another aspect, the present invention provides a pharmaceutical composition for preventing or treating diabetes, specifically, type 2 diabetes, comprising the compound represented by Formula 1 above or a pharmaceutically acceptable salt thereof as an active ingredient.

Preferably, the compound or pharmaceutically acceptable salt thereof enhances glucose metabolism.

As used herein, the term "prevention" refers to any action that would inhibit or delay the pathogenesis, spread, and recurrence of diabetes by administering the pharmaceutical composition, and the term "treatment" refers to any action that would improve or benefit the symptoms of diabetes by administering the pharmaceutical composition.

Advantageous Effect

The compound of novel amino-phenyl-sulfonyl-acetate derivatives of the present invention is effective in lowering blood glucose, and thus can be useful in the treatment of type 2 diabetes.

BRIEF DESCRIPTION OF DRAWING

The drawing shows the effect of lowering blood glucose according to the dose of the compound of Example 1 of the present invention.

Best Mode for Carrying Out Invention

Hereinbelow, the present invention will be described in detail with accompanying exemplary embodiments. However, the exemplary embodiments disclosed herein are only for illustrative purposes and should not be construed as limiting the scope of the present invention.

Various synthetic methods of the starting material for synthesizing the compound of the present invention are widely known, and if it is commercially available, it can be purchased from the suppliers and used. The reagent suppliers include Sigma-Aldrich, TCI, Wako, Kanto, Fluorochem, Acros, Alfa, Fluka, Dae-Jung, etc., but are not limited thereto. Further, all commercially available substances were used without further purification, unless defined otherwise.

First, the compounds used in the synthesis in Examples below were prepared as described in Preparation Examples below. The preparation examples are the examples of the compound represented by Formula 1 of Reaction 1, and may be variously modified according to the structure of the example to be prepared.

PREPARATION EXAMPLE 1

Preparation of 2-(4-((2'-methylbiphenyl-3-yl)methylamino)phenylsulfonyl)acetic acid (Path A)

Step 1-1) Preparation of methyl 2-(4-nitrophenylthio)acetate

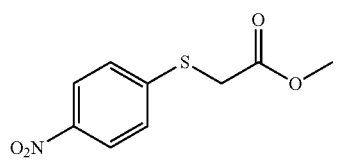

300 mL of N,N-dimethylformamide was added to 25.0 g (0.161 mol) of 4-nitrobenzenethiol. 18.5 mL (0.193 mmol) of methyl bromoacetate and 26.7 g (0.193 mol) of potassium carbonate were further added thereto. After stirring for 4 hours at 60° C., the mixture was cooled to room temperature. The layers were separated by adding 1 L of water and 800 mL of ethyl acetate and extracted with 400 mL of ethyl acetate. The thus-obtained organic layer was washed with 800 mL of saturated ammonium chloride aqueous solution twice, dried over anhydrous sodium sulfate, and concentrated. 22 g of the target compound was obtained by separation via silica column chromatography (EA:Hex=1:5).

$^1$H NMR (400 MHz, CDCl$_3$) δ 8.14 (d, 2H), 7.41 (d, 2H), 3.78 (s, 2H), 3.76 (s, 3H).

Step 1-2) Preparation of methyl 2-(4-nitrophenylsulfonyl)acetate

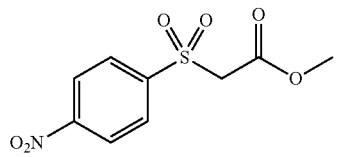

27.6 g (0.121 mol) of methyl 2-(4-nitrophenylthio)acetate obtained from Step 1-1) above was dissolved in 828 mL of dimethyl chloride. To this, 89.5 g (0.363 mol) of mCPBA was added as an oxidizing agent. The mixture was stirred for 6 hours at room temperature. The solid formed during stirring was filtered using dimethyl chloride. 1 L of a saturated sodium bicarbonate solution was added to the filtrate and stirred, and then the layers were separated. The organic layer was washed by adding 1 L of a 10% aqueous solution of sodium sulfite. Subsequently, the layer was washed with 1 L of saturated sodium bicarbonate, 1 L of water, and 500 mL of saturated sodium chloride solution in sequence. The thus-obtained organic layer was dried over magnesium sulfate. 30.0 g of the target compound was obtained, and was carried to the next reaction without purification.

Step 1-3) Preparation of methyl 2-(4-aminophenylsulfonyl)acetate

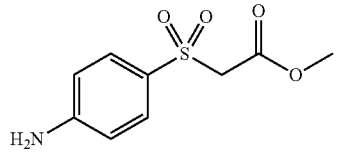

Methyl 2-(4-nitrophenylthio)acetate obtained from Step 1-2) above was dissolved in 600 mL of methanol and 150 mL of distilled water, and 19.5 g of iron and 61.5 g of ammonium chloride were added thereto. The mixture was stirred for 4 hours at 100° C. and cooled to room temperature. At 40° C., 300 mL of dimethyl chloride was added and impurities were filtered. The filtrate was dried over magnesium sulfate and concentrated, and 150 mL of dimethyl chloride was added thereto. The resultant was cooled and crystallized, and then filtered, and 15.5 g of the target compound was obtained.

Step 1-4) Preparation of methyl 2-(4-((2'-methylbiphenyl-3-yl)methylamino) phenylsulfonyl)acetate

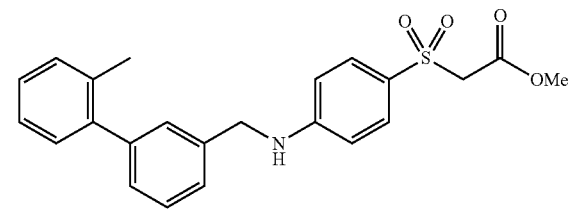 [SMILES: COC(=O)CS(=O)(=O)c1ccc(NCc2cccc(-c3ccccc3C)c2)cc1]

120 mL of dimethyl chloride was added to 8.0 g (34.9 mmol) of methyl 2-(4-aminophenylsulfonyl)acetate obtained from Step 1-3). 2'-Methylbiphenyl-3-carboxaldehyde (52.4 mmol) was added thereto. In addition, NaBH(OAc)$_3$ (70.0 mmol) and 8.0 mL of acetic acid were added. After stirring for 2 hours at room temperature, 120 mL of water was added. After separation, the organic layer was dried over magnesium sulfate and concentrated. 10.4 g of the target compound was obtained via silica column chromatography (EA:Hex=1:2).

$^1$H NMR (400 MHz, CDCl$_3$) δ 7.68 (d, 2H), 7.42 (t, 1H), 7.30-7.22 (m, 6H), 7.22-7.20 (m, 2H), 6.67 (d, 2H), 4.76 (s, 1H), 4.46 (d, 2H), 4.06 (s, 2H), 3.70 (s, 3H), 2.23 (s, 3H).

Step 1-5) Preparation of 2-(4-((2'-methylbiphenyl-3-yl)methylamino) phenylsulfonyl)acetic acid

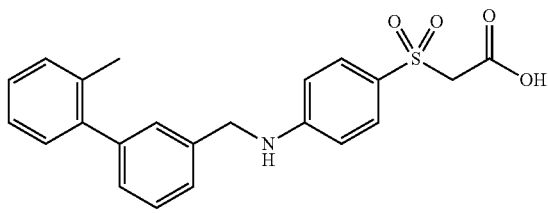 [SMILES: Cc1ccccc1-c1cccc(CNc2ccc(S(=O)(=O)CC(=O)O)cc2)c1]

340 mL of tetrahydrofuran, 254 mL of methanol, and 254 mL of water were added to 10.2 g (24.9 mmol) of methyl 2-(4-((2'-methylbiphenyl-3-yl)methylamino)phenylsulfonyl)acetate obtained from Step 1-4) above. 3.13 g of lithium hydroxide was further added thereto, and the mixture was stirred for 1 hour. The reaction solution was charged with a 1 N hydrochloric acid aqueous solution extracted with 1.5 L of ethyl acetate. The organic layer was washed with 400 mL of a saturated sodium chloride aqueous solution, dried over magnesium sulfate, and concentrated, and 9.5 g of the target compound was obtained.

$^1$H NMR (400 MHz, DMSO-d$_6$) δ 7.53 (d, 2H), 7.41 (t, 1H), 7.40-7.18 (m, 7H), 6.71 (d, 2H), 4.42 (d, 2H), 4.20 (s, 2H), 2.16 (s, 3H).

PREPARATION EXAMPLE 2

Preparation of 2-(4-(3-(benzofuran-5-yl)benzylamino)phenylsulfonyl)acetic acid (Path B)

Step 2-1) Preparation of methyl 2-(4-(3-bromobenzylamino)phenylsulfonyl)acetate

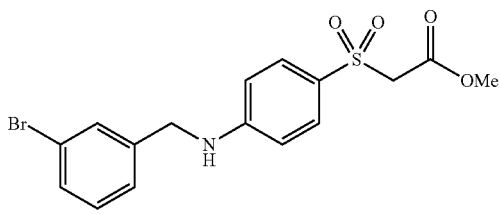 [SMILES: COC(=O)CS(=O)(=O)c1ccc(NCc2cccc(Br)c2)cc1]

12 mL of dimethyl chloride was added to 500 mg (2.18 mmol) of methyl 2-(4-aminophenylsulfonyl)acetate. 3-Bromobenzaldehyde was further added. 925 mg of NaBH(OAc)$_3$ was added, and 0.5 mL of acetic acid was further added thereto. The mixture was stirred for 2 hours at room temperature, and 12 mL of water was added. After separation, the organic layer was dried over magnesium sulfate and concentrated. Then, 560 mg of the target compound was obtained via column chromatography (EA:Hex=1:2).

$^1$H NMR (400 MHz, CDCl$_3$) δ 7.69 (d, 2H), 7.49 (s, 1H), 7.44 (d, 1H), 7.27-7.21 (m, 2H), 6.62 (d, 2H), 4.40 (s, 2H), 4.07 (s, 2H), 3.71 (s, 3H).

Step 2-2) Preparation of methyl 2-(4-(3-(benzofuran-5-yl)benzylamino)phenylsulfonyl)acetate

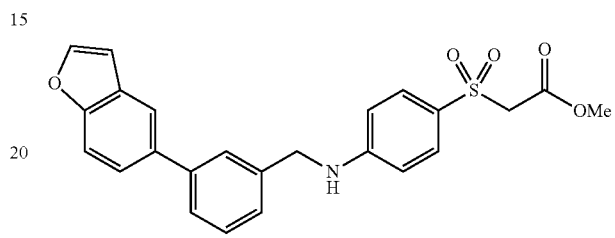

65 mg (0.164 mol) of methyl 2-(4-(3-bromobenzylamino)phenylsulfonyl)acetate obtained from Step 2-1) above was dissolved in 3 mL of a mixed solvent of dioxane:water (3:1), and 34 mg (0.214 mmol) of benzofuran-5-yl boronic acid, 9.5 mg of Pd(PPh$_3$)$_4$, and 45.3 mg of potassium carbonate were added thereto. Then, the mixture was stirred for 1 hour at 100° C., cooled to room temperature, and extracted with ethyl acetate and water. The product was dried over anhydrous magnesium sulfate, filtered, and concentrated under reduced pressure. The residue was separated via prep TLC (EA:Hex=1:1), and 5 mg of the target compound was obtained.

Step 2-3) Preparation of 2-(4-(3-(benzofuran-5-yl)benzylamino)phenylsulfonyl)acetic acid

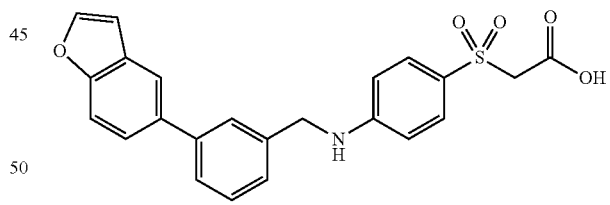

1.5 mL of tetrahydrofuran, 1.0 mL of methanol, and 1.0 mL of water were added to 81.2 mg (0.19 mmol) of methyl 2-(4-(3-(benzofuran-5-yl)benzylamino)phenylsulfonyl)acetate obtained from Step 2-2) above. 81.2 mg of lithium hydroxide was added thereto, and the mixture was stirred for 1 hour. The reaction solution was charged with 3 mL of a 1 N hydrochloric acid aqueous solution and extracted with 10 mL of ethyl acetate. The organic layer was washed with 3 mL of a saturated sodium chloride aqueous solution, dried over magnesium sulfate, and concentrated, and 32 mg of the target compound was obtained.

$^1$H NMR (400 MHz, DMSO-d$_6$) δ 8.03 (s, 1H), 7.90 (s, 1H), 7.68 (d, 2H), 7.56-7.52 (m, 4H), 7.45-7.32 (m, 3H), 7.01 (s, 1H), 6.73 (d, 2H), 4.44 (s, 2H), 4.21 (s, 2H).

PREPARATION EXAMPLE 3

Preparation of 2-(4-((2'-methylbiphenyl-3-yl)methylamino)phenylsulfinyl)acetic acid

Step 3-1) Preparation of methyl 2-(4-nitrophenylsulfinyl)acetate

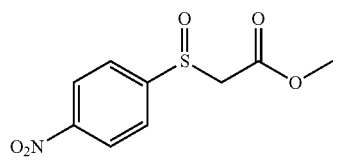 [SMILES: COC(=O)CS(=O)c1ccc([N+](=O)[O-])cc1]

2.00 g (8.8 mmol) of methyl 2-(4-nitrophenylthio)acetate obtained from Step 1-1) above was dissolved in 40 mL of dimethyl chloride. 1.26 g (7.3 mmol) of mCPBA was added thereto as an oxidizing agent at −10° C. The mixture was stirred for 1 hour at −10° C. The solid formed during stirring was filtered using dimethyl chloride. 50 mL of saturated sodium bicarbonate solution was added to the filtrate and stirred, and then the layers were separated. The organic layer was washed by adding 50 mL of an aqueous solution of sodium chloride. Subsequently, the layer was sequentially washed with 50 mL of saturated sodium bicarbonate, 50 mL of water, and 50 mL of a saturated sodium chloride solution. The thus-obtained organic layer was dried over magnesium sulfate. 1.5 g of the target compound was obtained, and was carried to the next reaction without purification.

Step 3-2) Preparation of methyl 2-(4-aminophenylsulfinyl)acetate

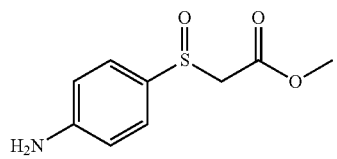

3.0 g of methyl 2-(4-nitrophenylsulfinyl)acetate obtained from Step 3-1) was dissolved in 60 mL of methanol and 15 mL of distilled water, and 2.07 g of iron and 6.65 g of ammonium chloride were added thereto. The mixture was stirred for 4 hours at 100° C. and cooled to room temperature. At 40° C., 30 mL of dimethyl chloride was added and impurities were filtered.

The filtrate was dried over magnesium sulfate and concentrated, and 15 mL of dimethyl chloride was added thereto. The resultant was cooled, crystallized, and then filtered, and 1.9 g of the target compound was obtained.

Step 3-3) Preparation of methyl 2-(4-((2'-methylbiphenyl-3-yl)methylamino)phenylsulfinyl)acetate

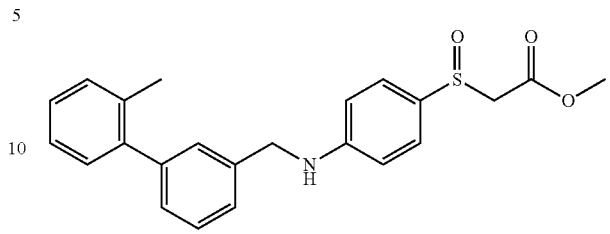

30 mL of dimethyl chloride was added to 1.20 g (56.3 mmol) methyl 2-(4-aminophenylsulfinyl)acetate obtained from Step 3-2) above. 84.5 mmol of 2'-methylbiphenyl-3-carboxaldehyde was added thereto. In addition, 112.6 mmol of NaBH(OAc)$_3$ and 1.2 mL of acetic acid were added. After stirring for 2 hours at room temperature, 30 mL of water was added. After the separation of layers, the organic layer was dried over magnesium sulfate and concentrated. 940 mg of the target compound was obtained via silica column chromatography (EA:Hex=1:2).

Step 3-4) Preparation of 2-(4-((2'-methylbiphenyl-3-yl)methylamino)phenylsulfinyl)acetic acid

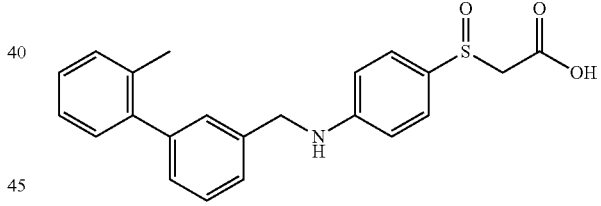

4.1 mL of tetrahydrofuran, 3.1 mL of methanol, and 3.1 mL of water were added to 95.2 mg (0.242 mmol) of methyl 2-(4-((2'-methylbiphenyl-3-yl)methylamino)phenylsulfinyl) acetate obtained from Step 3-3) above. 30.5 mg of lithium hydroxide was further added thereto, and the mixture was stirred for 1 hour. The reaction solution was charged with 10 mL of a 1 N hydrochloric acid aqueous solution and extracted with 10 mL of methylene chloride. The organic layer was dried over magnesium sulfate and concentrated, and 70 mg of the target compound was obtained.

$^1$H NMR (400 MHz, DMSO-d$_6$) δ 7.20-7.42 (m, 10H), 6.97 (bs, 1H), 6.72 (d, 2H), 4.39 (s, 2H), 3.76 (s, 2H), 2.16 (s, 3H).

EXAMPLE 1

Synthesis of 2-(4-((2'-methyl-biphenyl-3-yl)methylamino)phenylsulfonyl)acetic acid

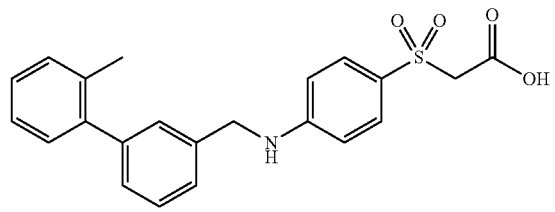 [SMILES: Cc1ccccc1-c1cccc(CNc2ccc(S(=O)(=O)CC(=O)O)cc2)c1]

The compound was obtained in the same manner as described in Preparation Example 1.
$^1$H NMR (400 MHz, DMSO-d$_6$) δ 7.53 (d, 2H), 7.41 (t, 1H), 7.40-7.18 (m, 7H), 6.71 (d, 2H), 4.42 (d, 2H), 4.20 (s, 2H), 2.16 (s, 3H).

EXAMPLE 2

Synthesis of 2-(4-(3-(benzofuran-5-yl)benzylamino)phenylsulfonyl)acetic acid

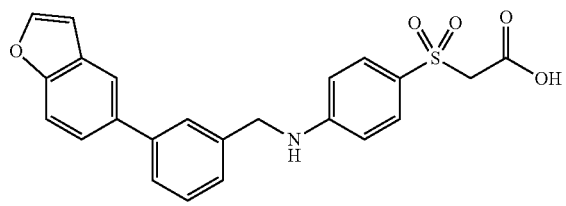 [SMILES: O=C(O)CS(=O)(=O)c1ccc(NCc2cccc(-c3ccc4occc4c3)c2)cc1]

The compound was obtained in the same manner as described in Preparation Example 2.
$^1$H NMR (400 MHz, DMSO-d$_6$) δ 8.03 (s, 1H), 7.90 (s, 1H), 7.68 (d, 2H), 7.56-7.52 (m, 4H), 7.45-7.32 (m, 3H), 7.01 (s, 1H), 6.73 (d, 2H), 4.44 (s, 2H), 4.21 (s, 2H).

EXAMPLE 3

Synthesis of 2-(4-(3-phenoxybenzylamino)phenylsulfonyl)acetic acid

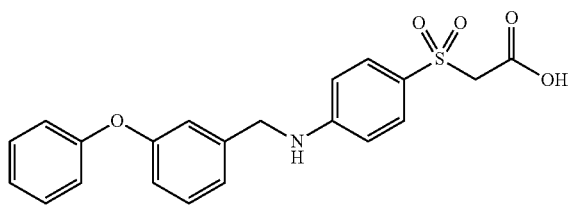 [SMILES: O=C(O)CS(=O)(=O)c1ccc(NCc2cccc(Oc3ccccc3)c2)cc1]

The compound was obtained in the same manner as described in Preparation Example 1.
$^1$H NMR (400 MHz, DMSO-d$_6$) δ 13.0 (bs, 1H), 7.52 (d, 2H), 7.40-7.25 (m, 4H), 7.14-7.11 (m, 2H), 7.05 (t, 3H), 6.87 (dd, 1H), 6.66 (d, 2H), 4.36 (d, 2H), 4.20 (s, 2H).

EXAMPLE 4

Synthesis of 2-(4-(3-bromobenzylamino)phenylsulfonyl)acetic acid

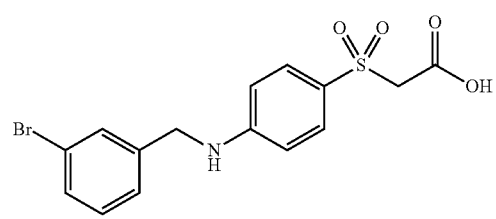 [SMILES: O=C(O)CS(=O)(=O)c1ccc(NCc2cccc(Br)c2)cc1]

The compound was obtained in the same manner as described in Preparation Example 1.
$^1$H NMR (400 MHz, DMSO-d$_6$) δ 7.55-7.54 (d, 3H), 7.44 (d, 1H), 7.36-7.30 (m, 3H), 6.68 (d, 2H), 4.38 (d, 2H), 4.20 (s, 2H).

EXAMPLE 5

Synthesis of 2-(4-((2',6'-dimethyl-4'-(3-(methylsulfonyl)propoxy)biphenyl-3-yl)methylamino)phenylsulfonyl)acetic acid

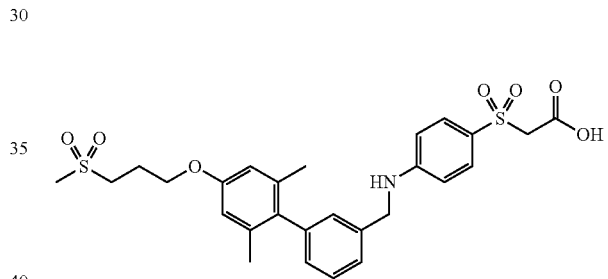

The compound was obtained in the same manner as described in Preparation Example 1.
$^1$H NMR (400 MHz, DMSO-d$_6$) δ 7.50 (d, 2H), 7.41 (t, 1H) 7.39 (d, 2H), 7.06 (s, 1H), 6.97 (d, 1H), 6.68 (t, 4H), 4.41 (s, 2H), 4.19 (s, 2H), 4.08 (t, 2H), 3.45 (t, 2H), 3.02 (s, 3H), 2.20-2.10 (m, 2H), 1.88 (s, 6H).

EXAMPLE 6

Synthesis of 2-(4-((2',6'-dimethylbiphenyl-3-yl)methylamino)phenylsulfonyl)acetic acid

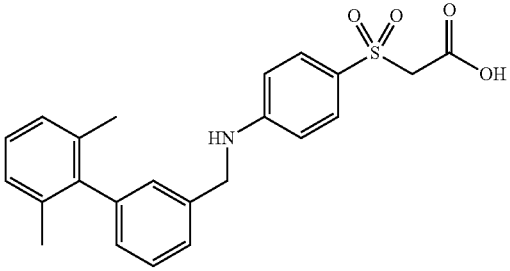 [SMILES: Cc1cccc(C)c1-c1cccc(CNc2ccc(S(=O)(=O)CC(=O)O)cc2)c1]

17

The compound was obtained in the same manner as described in Preparation Example 1.

¹H NMR (400 MHz, CDCl₃) δ 7.67 (d, 2H), 7.43 (t, 1H), 7.30 (d, 1H), 7.13-7.08 (m, 5H), 6.64 (d, 2H), 4.45 (s, 2H), 4.06 (s, 2H), 1.98 (s, 6H).

EXAMPLE 7

Synthesis of 2-(4-((4'-fluorobiphenyl-3-yl)methyl-amino)phenylsulfonyl)acetic acid

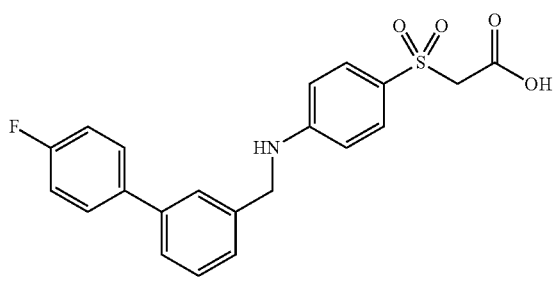 [SMILES: O=C(O)CS(=O)(=O)c1ccc(NCc2cccc(-c3ccc(F)cc3)c2)cc1]

The compound was obtained in the same manner as described in Preparation Example 1.

¹H NMR (400 MHz, DMSO-d₆) δ 8.3 (s, 1H), 7.70-7.64 (m, 3H), 7.52 (d, 3H), 7.43 (t, 1H), 7.40-7.27 (m, 7.32, 3H), 6.73 (d, 2H), 4.45 (s, 2H), 4.20 (s, 2H).

EXAMPLE 8

Synthesis of 2-(4-((3'-methoxybiphenyl-3-yl)methylamino)phenylsulfonyl)acetic acid

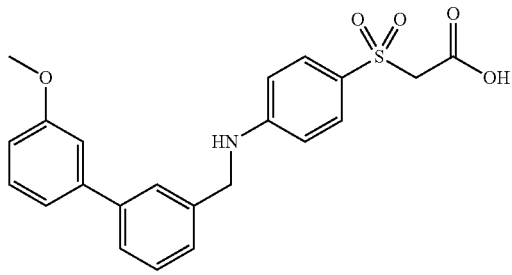 [SMILES: COc1cccc(-c2cccc(CNc3ccc(S(=O)(=O)CC(=O)O)cc3)c2)c1]

The compound was obtained in the same manner as described in Preparation Example 1.

¹H NMR (400 MHz, DMSO-d₆) δ 7.66 (s, 1H), 7.57-7.52 (m, 3H), 7.44-7.38 (m, 4H), 7.21-7.19 (m, 2H), 6.93 (d, 1H), 6.72 (d, 2H), 4.42 (s, 21), 4.20 (s, 2H), 3.83 (s, 3H).

18

EXAMPLE 9

Synthesis of 2-(4-((4-fluoro-2'-methylbiphenyl-3-yl)methylamino)phenylsulfonyl)acetic acid

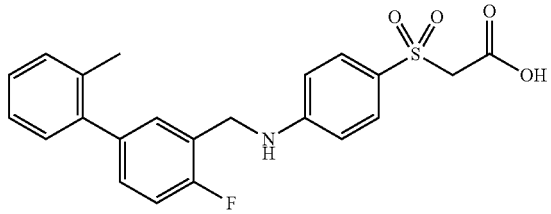 [SMILES: Cc1ccccc1-c1ccc(F)c(CNc2ccc(S(=O)(=O)CC(=O)O)cc2)c1]

The compound was obtained in the same manner as described in Preparation Example 2.

¹H NMR (400 MHz, CDCl₃) δ 7.56 (d, 2H), 7.14-7.00 (m, 7H), 6.50 (d, 2H), 4.30 (s, 2H), 3.94 (d, 2H), 2.06 (s, 3H).

EXAMPLE 10

Synthesis of 2-(4-((2',4-dimethylbiphenyl-3-yl)methylamino)phenylsulfonyl)acetic acid

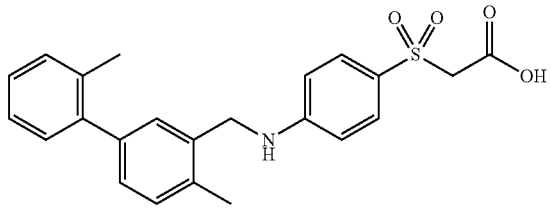 [SMILES: Cc1ccc(-c2ccccc2C)cc1CNc1ccc(S(=O)(=O)CC(=O)O)cc1]

The compound was obtained in the same manner as described in Preparation Example 2.

¹H NMR (400 MHz, DMSO-d₆) δ 7.51 (d, 2H), 7.28-7.00 (m, 8H), 6.67 (d, 2H), 4.34 (d, 2H), 3.81 (s, 2H), 2.37 (s, 3H), 2.10 (s, 3H).

EXAMPLE 11

Synthesis of 2-(4-((4-methoxy-2'-methylbiphenyl-3-yl)methylamino)phenylsulfonyl)acetic acid

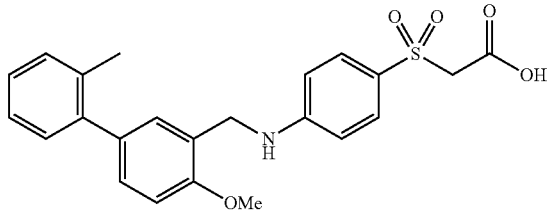 [SMILES: COc1ccc(-c2ccccc2C)cc1CNc1ccc(S(=O)(=O)CC(=O)O)cc1]

The compound was obtained in the same manner as described in Preparation Example 2.

¹H NMR (400 MHz, DMSO-d₆) δ 7.51 (d, 2H), 7.20-7.07 (m, 8H), 6.67 (d, 2H), 4.34 (d, 2H), 4.12 (s, 2H), 3.89 (s, 3H), 2.09 (s, 3H).

EXAMPLE 12

Synthesis of 2-(4-((2-fluoro-2'-methylbiphenyl-3-yl)methylamino)phenylsulfonyl)acetic acid

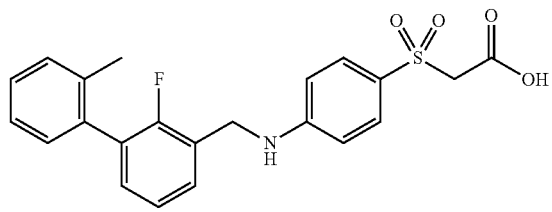 [SMILES: Cc1ccccc1-c1cccc(CNc2ccc(S(=O)(=O)CC(=O)O)cc2)c1F]

The compound was obtained in the same manner as described in Preparation Example 2.

$^1$H NMR (400 MHz, DMSO-d$_6$) δ 7.55 (d, 2H), 7.39-7.20 (m, 8H), 6.73 (d, 2H), 4.45 (d, 2H), 4.17 (s, 2H), 2.14 (s, 3H).

EXAMPLE 13

Synthesis of 2-(4-((2-methoxy-2'-methylbiphenyl-3-yl)methylamino)phenylsulfonyl)acetic acid

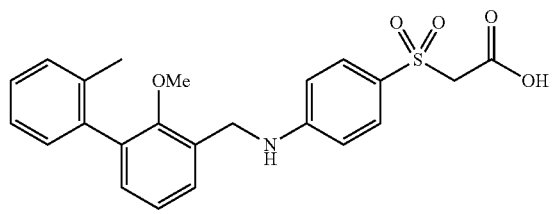 [SMILES: COc1c(CNc2ccc(S(=O)(=O)CC(=O)O)cc2)cccc1-c1ccccc1C]

The compound was obtained in the same manner as described in Preparation Example 2.

$^1$H NMR (400 MHz, DMSO-d$_6$) δ 7.54 (d, 2H), 7.30-7.22 (m, 5H), 7.21-7.06 (m, 3H), 6.66 (d, 2H), 4.39 (d, 2H), 3.76 (s, 3H), 3.29 (s, 3H), 2.12 (s, 3H).

EXAMPLE 14

Synthesis of 2-(4-((4-fluoro-2',3'-dimethylbiphenyl-3-yl)methylamino)phenylsulfonyl)acetic acid

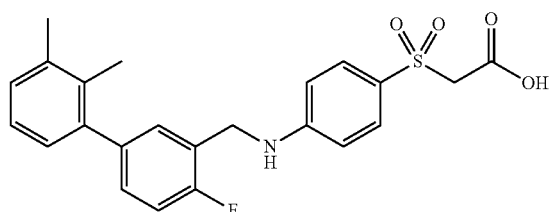

The compound was obtained in the same manner as described in Preparation Example 2.

$^1$H NMR (400 MHz, CDCl$_3$) δ 7.66 (d, 2H), 7.20-6.96 (m, 6H), 4.41 (s, 2H), 4.01 (d, 2H), 2.32 (s, 3H), 2.02 (s, 3H).

EXAMPLE 15

Synthesis of 2-(4-((4-fluoro-2',4'-dimethylbiphenyl-3-yl)methylamino)phenylsulfonyl)acetic acid

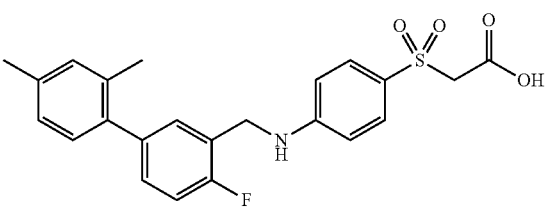 [SMILES: Cc1ccc(-c2ccc(F)c(CNc3ccc(S(=O)(=O)CC(=O)O)cc3)c2)c(C)c1]

The compound was obtained in the same manner as described in Preparation Example 2.

$^1$H NMR (400 MHz, DMSO-d$_6$) δ 7.52 (d, 2H), 7.30-7.23 (m, 3H), 7.16-7.13 (m, 1H), 7.06-7.02 (m, 3H), 6.68 (d, 2H), 4.43 (d, 2H), 3.86 (s, 2H), 2.27 (s, 3H), 2.07 (s, 3H).

EXAMPLE 16

Synthesis of 2-(4-((2-fluorobiphenyl-3-yl)methylamino)phenylsulfonyl)acetic acid

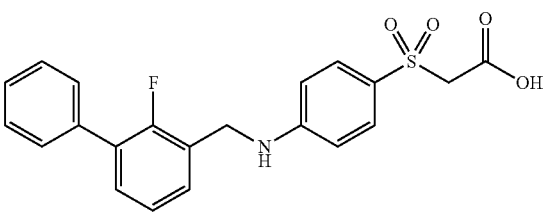 [SMILES: O=C(O)CS(=O)(=O)c1ccc(NCc2cccc(-c3ccccc3)c2F)cc1]

The compound was obtained in the same manner as described in Preparation Example 2.

$^1$H NMR (400 MHz, DMSO-d$_6$) δ 7.56-7.54 (m, 4H), 7.51-7.49 (m, 2H), 7.47-7.35 (m, 3H), 7.32-7.24 (m, 2H), 6.73 (d, 2H), 4.46 (d, 2H), 4.17 (s, 3H).

EXAMPLE 17

Synthesis of 2-(4-((2-methoxybiphenyl-3-yl)methylamino)phenylsulfonyl)acetic acid

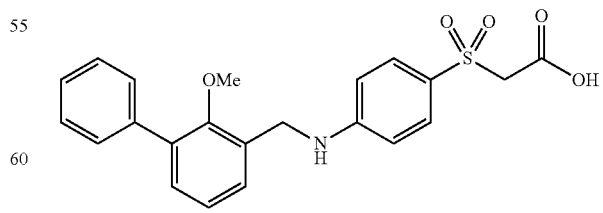

The compound was obtained in the same manner as described in Preparation Example 2.

$^1$H NMR (400 MHz, DMSO-d$_6$) δ 7.57-7.52 (m, 4H), 7.48-7.45 (m, 2H), 7.40-7.36 (m, 1H), 7.31-7.25 (m, 2H), 7.19-7.15 (m, 1H), 7.12-7.09 (m, 1H), 6.67 (d, 2H), 4.41 (d, 2H), 3.81 (s, 2H), 3.35 (s, 3H).

EXAMPLE 18

Synthesis of 2-(4-((4-methoxy-2',3'-dimethylbiphenyl-3-yl)methylamino)phenylsulfonyl)acetic acid

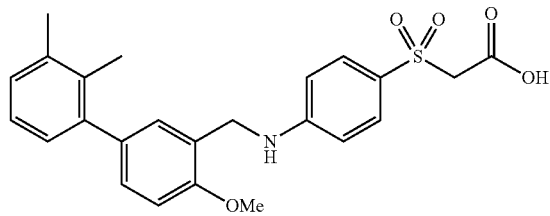 [SMILES: COc1ccc(-c2cccc(C)c2C)cc1CNc1ccc(S(=O)(=O)CC(=O)O)cc1]

The compound was obtained in the same manner as described in Preparation Example 2.

$^1$H NMR (400 MHz, DMSO-d$_6$) δ 7.51 (d, 2H), 7.18-7.05 (m, 6H), 6.94-6.92 (m, 1H), 6.66 (d, 2H), 4.34 (d, 2H), 4.09 (2H), 3.88 (s, 3H), 2.23 (s, 3H), 1.97 (s, 3H).

EXAMPLE 19

Synthesis of 2-(4-(2-methoxybenzylamino)phenylsulfonyl)acetic acid

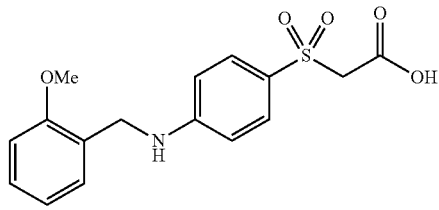 [SMILES: COc1ccccc1CNc1ccc(S(=O)(=O)CC(=O)O)cc1]

The compound was obtained in the same manner as described in Preparation Example 2.

$^1$H NMR (400 MHz, DMSO-d$_6$) δ 7.51 (d, 2H), 7.27-7.19 (m, 2H), 7.01 (d, 1H), 6.89 (t, 1H), 6.65 (d, 2H), 4.29 (s, 2H), 4.20 (s, 2H), 3.83 (s, 3H).

EXAMPLE 20

Synthesis of 2-(4-(3-methoxybenzylamino)phenylsulfonyl)acetic acid

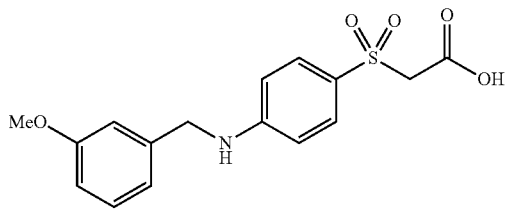 [SMILES: COc1cccc(CNc2ccc(S(=O)(=O)CC(=O)O)cc2)c1]

The compound was obtained in the same manner as described in Preparation Example 2.

$^1$H NMR (400 MHz, DMSO-d$_6$) δ 7.52 (d, 2H), 7.31-7.22 (m, 2H), 6.93-6.91 (m, 1H), 6.82-6.80 (m, 1H), 6.64 (d, 2H), 4.31 (d, 2H), 3.86 (s, 2H), 3.72 (s, 3H).

EXAMPLE 21

Synthesis of 2-(4-(2-methylbenzylamino)phenylsulfonyl)acetic acid

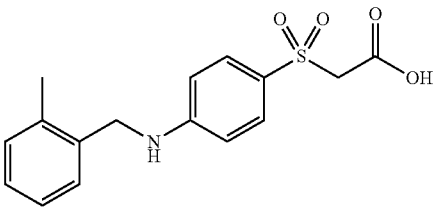 [SMILES: Cc1ccccc1CNc1ccc(S(=O)(=O)CC(=O)O)cc1]

The compound was obtained in the same manner as described in Preparation Example 2.

$^1$H NMR (400 MHz, DMSO-d$_6$) δ 7.54 (d, 2H), 7.24-7.10 (m, 4H), 6.66 (d, 2H), 4.28 (d, 2H), 3.88 (s, 2H), 2.32 (s, 3H).

EXAMPLE 22

Synthesis of 2-(4-(4-ethoxybenzylamino)phenylsulfonyl)acetic acid

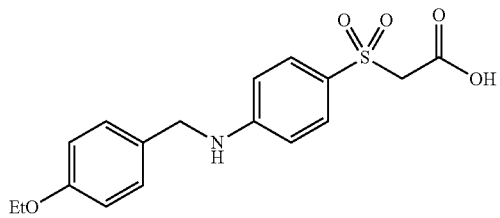 [SMILES: CCOc1ccc(CNc2ccc(S(=O)(=O)CC(=O)O)cc2)cc1]

The compound was obtained in the same manner as described in Preparation Example 2.

$^1$H NMR (400 MHz, DMSO-d$_6$) δ 7.52-7.48 (m, 2H), 7.25 (d, 2H), 6.88 (d, 2H), 6.69-6.62 (m, 2H), 4.28 (d, 2H), 4.20 (s, 2H), 3.98 (q, 2H), 1.28 (t, 3H).

EXAMPLE 23

Synthesis of 2-(4-(furan-3-yl-methylamino)phenylsulfonyl)acetic acid

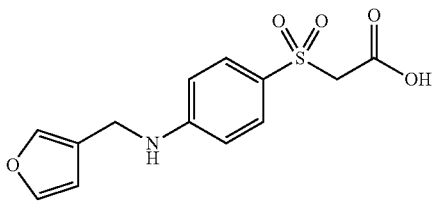 [SMILES: O=C(O)CS(=O)(=O)c1ccc(NCc2ccoc2)cc1]

The compound was obtained in the same manner as described in Preparation Example 2.

$^1$H NMR (400 MHz, DMSO-d$_6$) δ 7.64-7.61 (m, 2H), 7.53 (d, 2H), 7.05 (t, 1H), 6.71 (d, 2H), 6.47 (s, 1H), 4.21 (s, 2H), 4.16 (d, 2H).

EXAMPLE 24

Synthesis of 2-(4-(3-(pyridin-3-yl)benzylamino)phenylsulfonyl)acetic acid

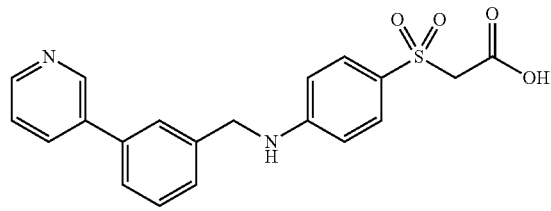 [SMILES: O=C(O)CS(=O)(=O)c1ccc(NCc2cccc(-c3cccnc3)c2)cc1]

The compound was obtained in the same manner as described in Preparation Example 2.

$^1$H NMR (400 MHz, CDCl$_3$) δ 8.76 (s, 1H), 8.55-8.54 (m, 1H), 7.99 (d, 1H), 7.65 (d, 2H), 7.56 (s, 1H), 7.50-7.37 (m, 4H), 6.68 (d, 2H), 4.49 (s, 2H), 4.00 (d, 2H).

EXAMPLE 25

Synthesis of 2-(4-(3-(pyridin-4-yl)benzylamino)phenylsulfonyl)acetic acid

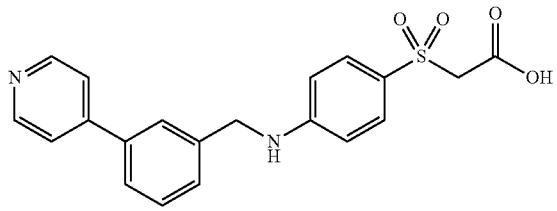 [SMILES: O=C(O)CS(=O)(=O)c1ccc(NCc2cccc(-c3ccncc3)c2)cc1]

The compound was obtained in the same manner as described in Preparation Example 2.

$^1$H NMR (400 MHz, MeOD-d$_4$) δ 8.77 (d, 2H), 8.18 (d, 2H), 7.88-7.78 (m, 2H), 7.63-7.60 (m, 4H), 6.72 (d, 2H), 4.56 (s, 2H), 4.12 (s, 2H).

EXAMPLE 26

Synthesis of 2-(4-(3-(benzo[d][1,3]dioxol-5-yl)benzylamino)phenylsulfonyl)acetic acid

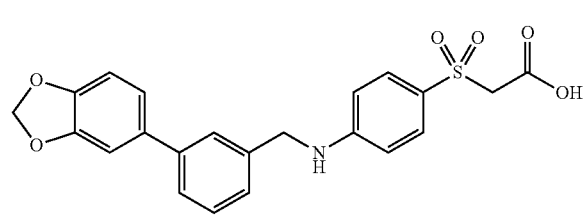 [SMILES: O=C(O)CS(=O)(=O)c1ccc(NCc2cccc(-c3ccc4c(c3)OCO4)c2)cc1]

The compound was obtained in the same manner as described in Preparation Example 2.

$^1$H NMR (400 MHz, MeOD-d$_4$) δ 7.62 (d, 2H), 7.51 (s, 1H), 8.18 (d, 2H), 7.88-7.78 (m, 2H), 7.63-7.60 (m, 4H), 6.72 (d, 2H), 4.56 (s, 2H), 4.12 (s, 2H).

EXAMPLE 27

Synthesis of 2-(4-(3-(2,2-difluoro-benzo[d][1,3]dioxol-5-yl)benzylamino)phenylsulfonyl)acetic acid

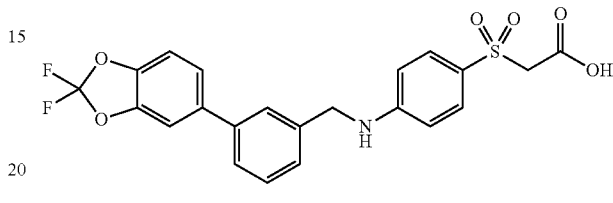

The compound was obtained in the same manner as described in Preparation Example 2.

$^1$H NMR (400 MHz, DMSO-d$_6$) δ 7.76 (s, 1H), 7.73 (s, 1H), 7.56-7.49 (m, 5H), 7.44 (t, 1H), 7.37-7.32 (m, 2H), 6.71 (d, 2H), 4.42 (s, 2H), 4.20 (s, 2H).

EXAMPLE 28

Synthesis of 2-(4-(3-(4-fluoro-benzo[d][1,3]dioxol-5-yl)benzylamino)phenylsulfonyl)acetic acid

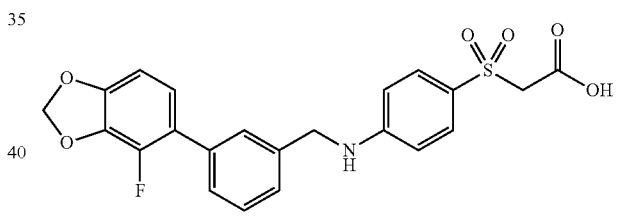

The compound was obtained in the same manner as described in Preparation Example 2.

$^1$H NMR (400 MHz, DMSO-d$_6$) δ 7.54 (d, 2H), 7.47-7.30 (m, 4H), 7.00-6.91 (m, 2H), 6.71 (d, 2H), 6.17 (s, 2H), 4.41 (s, 2H), 4.20 (s, 2H).

EXAMPLE 29

Synthesis of 2-(4-(3-(2,3-dihydrobenzo[b][1,4]dioxin-6-yl)benzylamino)phenylsulfonyl)acetic acid

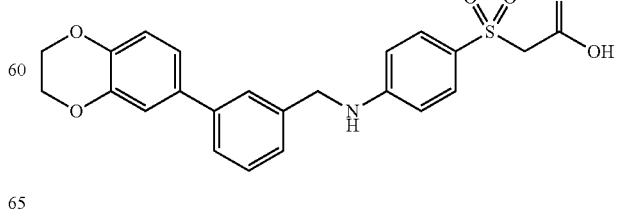

The compound was obtained in the same manner as described in Preparation Example 2.

¹H NMR (400 MHz, DMSO-d₆) δ 7.63 (s, 1H), 7.52 (d, 2H), 7.47 (d, 1H), 7.39 (t, 1H), 7.28 (d, 1H), 7.13-7.10 (m, 2H), 6.93 (d, 1H), 6.71 (d, 2H), 4.43 (s, 2H), 7.27 (s, 4H), 4.20 (s, 2H).

EXAMPLE 30

Synthesis of 2-(4-(3-(2-methylpyridin-4-yl)benzylamino)phenylsulfonyl)acetic acid

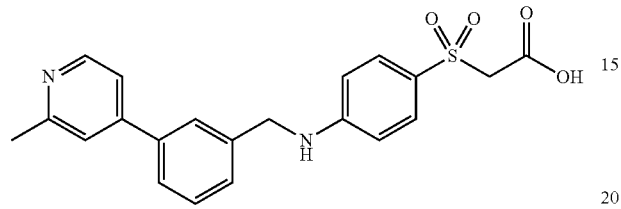

The compound was obtained in the same manner as described in Preparation Example 2.
¹H NMR (400 MHz, DMSO-d₆) δ 8.49 (d, 2H), 7.86 (s, 1H), 7.67-7.35 (m, 6H), 6.69 (d, 2H), 4.47 (d, 2H), 3.88 (s, 2H), 2.52 (s, 3H).

EXAMPLE 31

Synthesis of 2-(4-(3-(2-hydroxypyridin-4-yl)benzylamino)phenylsulfonyl)acetic acid

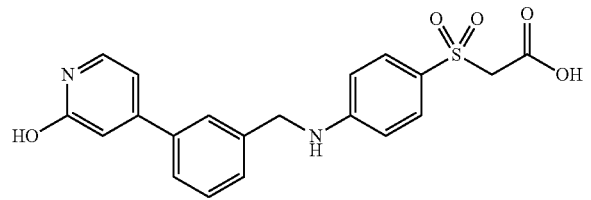 [SMILES: O=C(O)CS(=O)(=O)c1ccc(NCc2cccc(-c3ccnc(O)c3)c2)cc1]

The compound was obtained in the same manner as described in Preparation Example 2.
¹H NMR (400 MHz, DMSO-d₆) δ 8.49 (d, 2H), 7.86 (s, 1H), 7.67-7.35 (m, 6H), 6.69 (d, 2H), 4.47 (d, 2H), 3.88 (s, 2H), 2.52 (s, 3H).

EXAMPLE 32

Synthesis of 2-(4-(3-(2-methoxypyridin-4-yl)benzylamino)phenylsulfonyl)acetic acid

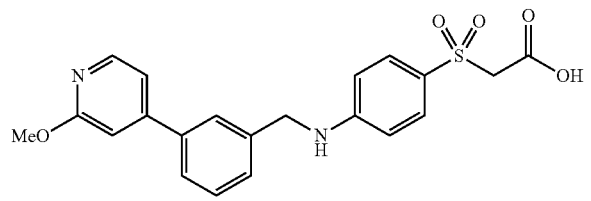 [SMILES: COc1cc(-c2cccc(CNc3ccc(S(=O)(=O)CC(=O)O)cc3)c2)ccn1]

The compound was obtained in the same manner as described in Preparation Example 2.

¹H NMR (400 MHz, DMSO-d₆) δ 8.22 (d, 1H), 7.80 (s, 1H), 7.66-7.65 (m, 1H), 7.53 (d, 2H), 7.48-7.29 (m, 5H), 7.09 (s, 1H), 6.70 (d, 2H), 7.42 (d, 2H), 3.89 (s, 3H), 3.87 (s, 2H).

EXAMPLE 33

Synthesis of 2-(4-(3-(2-ethoxypyridin-4-yl)benzylamino)phenylsulfonyl)acetic acid

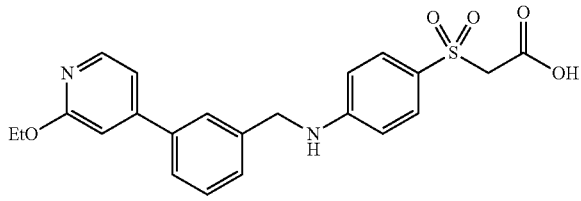 [SMILES: CCOc1cc(-c2cccc(CNc3ccc(S(=O)(=O)CC(=O)O)cc3)c2)ccn1]

The compound was obtained in the same manner as described in Preparation Example 2.
¹H NMR (400 MHz, DMSO-d₆) δ 8.22 (d, 1H), 7.79-7.67 (m, 2H), 7.53 (d, 2H), 7.45-7.42 (m, 2H), 7.30-7.26 (m, 2H), 7.07 (s, 1H), 6.69 (d, 2H), 4.42 (d, 2H), 4.34 (q, 2H), 3.84 (s, 2H), 1.35 (t, 3H).

EXAMPLE 34

Synthesis of 2-(4-((4'-methylbiphenyl-3-yl)methylamino)phenylsulfonyl)acetic acid

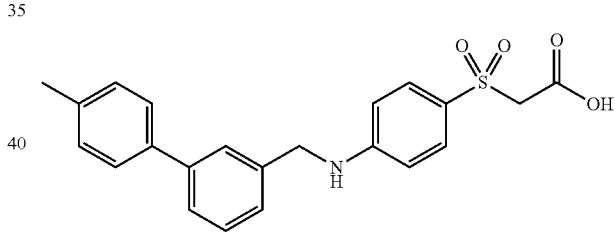

The compound was obtained in the same manner as described in Preparation Example 2.
¹H NMR (400 MHz, DMSO-d₆) δ 7.63 (m, 1H), 7.58-7.50 (m, 5H), 7.40 (t, 1H), 7.32-7.26 (m, 3H), 6.72 (d, 2H), 4.42 (d, 2H), 4.20 (s, 2H), 2.33 (s, 3H).

EXAMPLE 35

Synthesis of 2-(4-(biphenyl-3-yl-methylamino)phenylsulfonyl)acetic acid

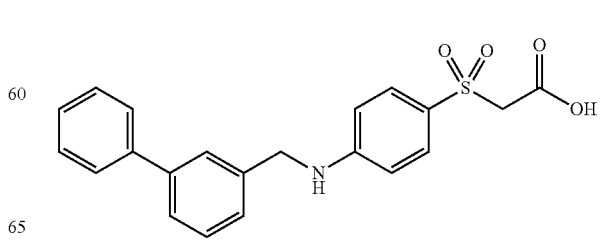

The compound was obtained in the same manner as described in Preparation Example 2.

$^1$H NMR (400 MHz, CDCl$_3$) δ 7.73 (d, 2H), 7.58-7.52 (m, 4H), 7.44 (m, 3H), 7.37-7.25 (m, 2H), 6.69 (d, 2H), 4.46 (s, 2H), 4.04 (s, 2H).

EXAMPLE 36

Synthesis of 2-(4-((3',4'-dimethylbiphenyl-3-yl)methylamino)phenylsulfonyl)acetic acid

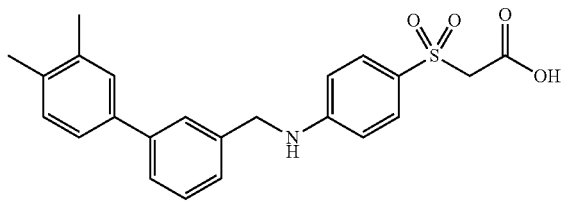 [SMILES: Cc1ccc(-c2cccc(CNc3ccc(S(=O)(=O)CC(=O)O)cc3)c2)cc1C]

The compound was obtained in the same manner as described in Preparation Example 2.

$^1$H NMR (400 MHz, CDCl$_3$) δ 7.64 (d, 2H), 7.50-7.46 (m, 2H), 7.37-7.33 (m, 2H), 7.28 (d, 1H), 7.22 (d, 1H), 7.16 (d, 1H), 6.65 (d, 2H), 4.43 (s, 2H), 4.00 (s, 2H), 2.29 (s, 3H), 2.27 (s, 3H).

EXAMPLE 37

Synthesis of 2-(4-((2',4'-dimethylbiphenyl-3-yl)methylamino)phenylsulfonyl)acetic acid

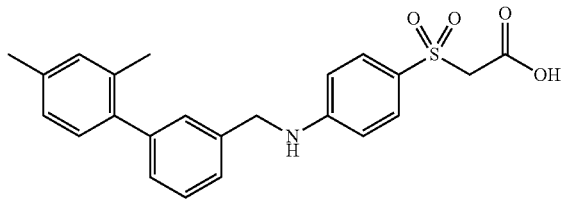 [SMILES: Cc1ccc(-c2cccc(CNc3ccc(S(=O)(=O)CC(=O)O)cc3)c2)c(C)c1]

The compound was obtained in the same manner as described in Preparation Example 2.

$^1$H NMR (400 MHz, DMSO-d$_6$) δ 7.52 (d, 2H), 7.41-7.28 (m, 3H), 7.19 (d, 2H), 7.08-7.02 (m, 3H), 6.70 (d, 2H), 4.40 (d, 2H), 4.18 (s, 2H), 2.29 (s, 3H), 2.14 (s, 3H).

EXAMPLE 38

Synthesis of 2-(4-((2',3'-dimethylbiphenyl-3-yl)methylamino)phenylsulfonyl)acetic acid

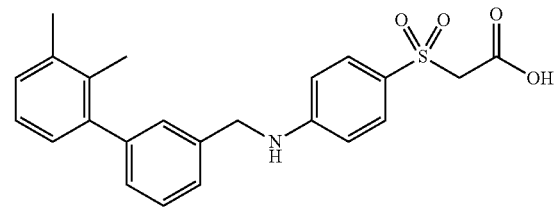 [SMILES: Cc1cccc(-c2cccc(CNc3ccc(S(=O)(=O)CC(=O)O)cc3)c2)c1C]

The compound was obtained in the same manner as described in Preparation Example 2.

$^1$H NMR (400 MHz, DMSO-d$_6$) δ 7.52 (d, 2H), 7.40 (t, 1H), 7.33 (d, 1H), 7.26 (s, 1H), 7.18-7.14 (m, 3H), 7.11 (d, 2H), 7.99 (d, 1H), 6.71 (d, 2H), 4.41 (s, 2H), 4.20 (s, 2H), 2.27 (s, 3H), 2.05 (s, 3H).

EXAMPLE 39

Synthesis of 2-(4-((2',5'-dimethylbiphenyl-3-yl)methylamino)phenylsulfonyl)acetic acid

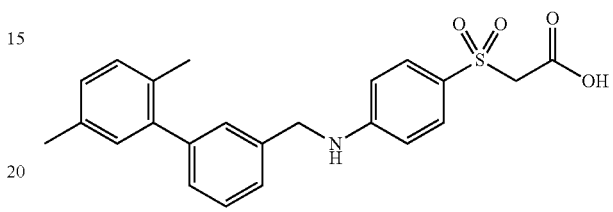

The compound was obtained in the same manner as described in Preparation Example 2.

$^1$H NMR (400 MHz, DMSO-d$_6$) δ 7.52 (d, 2H), 7.40 (t, 1H), 7.38-7.29 (m, 2H), 7.18 (d, 1H), 7.15 (d, 1H), 7.06 (d, 1H), 7.02 (s, 1H), 6.71 (d, 2H), 4.41 (s, 2H), 4.22 (s, 2H), 2.28 (s, 3H), 2.12 (s, 3H).

EXAMPLE 40

Synthesis of 2-(4-((4'-ethylbiphenyl-3-yl-methylamino)phenylsulfonyl)acetic acid

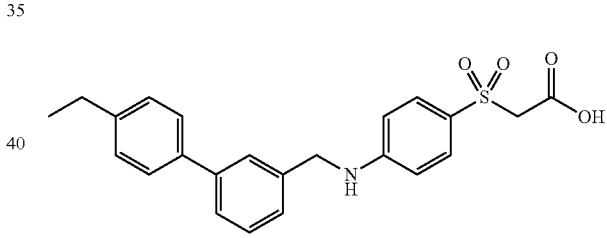

The compound was obtained in the same manner as described in Preparation Example 2.

$^1$H NMR (400 MHz, CDCl$_3$) δ 7.70 (d, 2H), 7.49-7.46 (m, 2H), 7.42 (d, 2H), 7.33 (t, 1H), 7.22-7.20 (m, 3H), 6.94 (d, 2H), 4.42 (s, 2H), 3.99 (s, 2H), 2.62 (q, 2H), 1.22 (t, 3H).

EXAMPLE 41

Synthesis of 2-(4-((2'-ethylbiphenyl-3-yl)methylamino)phenylsulfonyl)acetic acid

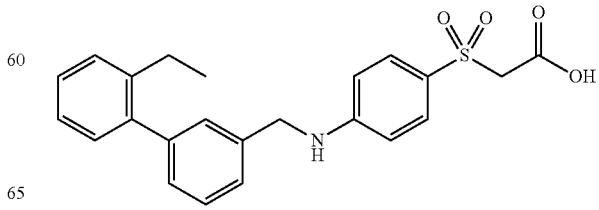

The compound was obtained in the same manner as described in Preparation Example 2.

$^1$H NMR (400 MHz, DMSO-d$_6$) δ 7.51 (d, 2H), 7.43-7.34 (m, 2H), 7.37-7.27 (m, 3H), 7.25-7.17 (m, 3H), 6.70 (d, 2H), 4.42 (s, 2H), 4.20 (s, 2H), 2.48 (q, 2H), 0.94 (t, 3H).

EXAMPLE 42

Synthesis of 2-(4-((3',5'-dimethylbiphenyl-3-yl)methylamino)phenylsulfonyl)acetic acid

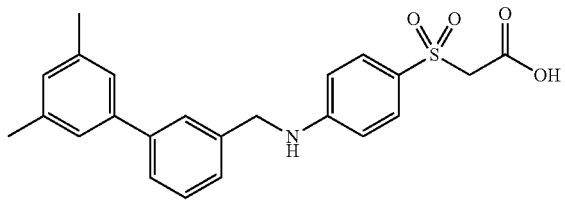 [SMILES: Cc1cc(C)cc(-c2cccc(CNc3ccc(S(=O)(=O)CC(=O)O)cc3)c2)c1]

The compound was obtained in the same manner as described in Preparation Example 2.

$^1$H NMR (400 MHz, DMSO-d$_6$) δ 7.63 (s, 1H), 7.40 (t, 1H), 7.53-7.50 (m, 3H), 7.40 (t, 1H), 7.32 (d, 1H), 7.24 (m, 2H), 6.72 (d, 2H), 4.42 (s, 2H), 4.20 (s, 2H), 2.33 (s, 6H).

EXAMPLE 43

Synthesis of 2-(4-((4'-methoxy-2'-methylbiphenyl-3-yl)methylamino)phenysulfonyl)acetic acid

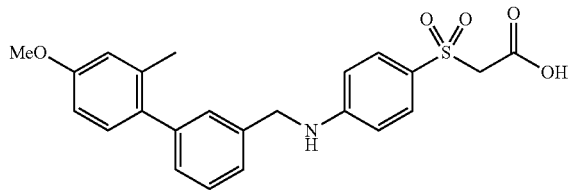 [SMILES: COc1ccc(-c2cccc(CNc3ccc(S(=O)(=O)CC(=O)O)cc3)c2)c(C)c1]

The compound was obtained in the same manner as described in Preparation Example 2.

$^1$H NMR (400 MHz, DMSO-d$_6$) δ 7.53-7.50 (m, 2H), 7.40-7.36 (m, 1H), 7.31-7.24 (m, 2H), 7.18 (d, 1H), 7.09 (d, 1H), 6.85-6.80 (m, 2H), 6.72-6.67 (m, 2H), 4.41 (d, 2H), 4.20 (s, 2H), 3.76 (s, 3H), 2.16 (s, 3H).

EXAMPLE 44

Synthesis of 2-(4-((4'-methoxy-2',6'-dimethylbiphenyl-3-yl)methylamino)phenylsulfonyl)acetic acid

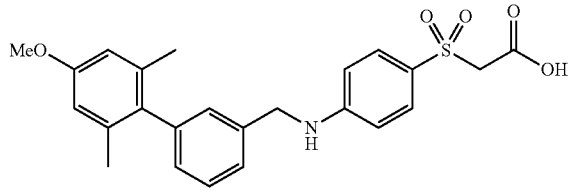

The compound was obtained in the same manner as described in Preparation Example 2.

$^1$H NMR (400 MHz, DMSO-d$_6$) δ 7.52 (d, 2H), 7.45-7.38 (m, 2H), 7.06-6.98 (m, 2H), 6.73-6.67 (m, 4H), 4.39 (s, 2H), 4.20 (s, 2H), 3.73 (s, 3H), 1.85 (s, 6H).

EXAMPLE 45

Synthesis of 2-(4-((3'-methylbiphenyl-3-yl)methylamino)phenylsulfonyl)acetic acid

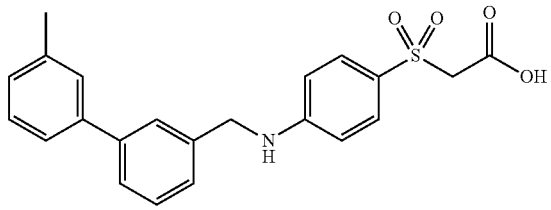 [SMILES: Cc1cccc(-c2cccc(CNc3ccc(S(=O)(=O)CC(=O)O)cc3)c2)c1]

The compound was obtained in the same manner as described in Preparation Example 2.

$^1$H NMR (400 MHz, DMSO-d$_6$) δ 7.65 (s, 2H), 7.54-7.50 (m, 3H), 7.46 (s, 1H), 7.44-7.40 (m, 2H), 7.18 (d, 1H), 6.72 (d, 2H), 4.42 (s, 2H), 4.20 (s, 2H), 2.37 (s, 3H).

EXAMPLE 46

Synthesis of 2-(4-((3',4'-dimethoxybiphenyl-3-yl)methylamino)phenylsulfonyl)acetic acid

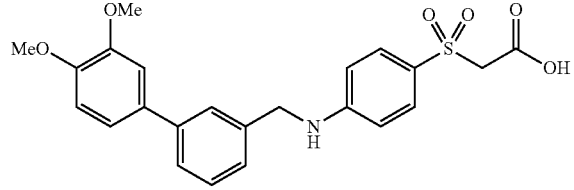 [SMILES: COc1ccc(-c2cccc(CNc3ccc(S(=O)(=O)CC(=O)O)cc3)c2)cc1OC]

The compound was obtained in the same manner as described in Preparation Example 2.

$^1$H NMR (400 MHz, DMSO-d$_6$) δ 7.63-7.52 (m, 3H), 7.41-7.33 (m, 2H), 7.28 (d, 1H), 7.18-7.16 (m, 2H), 7.03 (d, 1H), 6.72 (d, 2H), 4.41 (d, 2H), 4.15 (s, 2H), 3.82 (s, 3H), 3.78 (s, 3H).

EXAMPLE 47

Synthesis of 2-(4-((4'-chloro-2'-methylbiphenyl-3-yl)methylamino)phenylsulfonyl)acetic acid

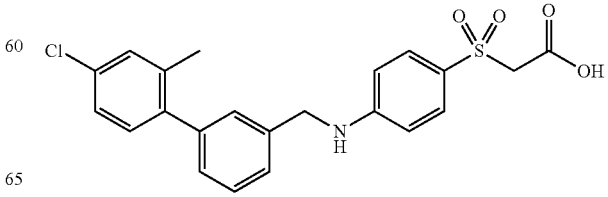

The compound was obtained in the same manner as described in Preparation Example 2.

¹H NMR (400 MHz, DMSO-d₆) δ 7.52 (d, 2H), 7.42 (t, 1H), 7.38-7.29 (m, 4H), 7.21 (t, 2H), 6.70 (d, 2H), 4.42 (d, 2H), 4.20 (s, 2H), 2.17 (s, 3H).

EXAMPLE 48

Synthesis of 2-(4-((4'-chloro-2'-(trifluoromethyl) biphenyl-3-yl)methylamino)phenylsulfonyl)acetic acid

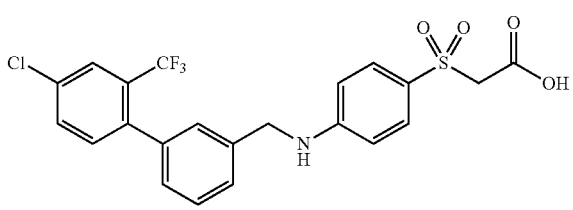 [SMILES: O=C(O)CS(=O)(=O)c1ccc(NCc2cccc(-c3ccc(Cl)cc3C(F)(F)F)c2)cc1]

The compound was obtained in the same manner as described in Preparation Example 2.

¹H NMR (400 MHz, DMSO-d₆) δ 7.90 (d, 1H), 7.80 (dd, 1H), 7.51 (d, 2H), 7.45-7.36 (m, 3H), 7.30 (s, 1H), 7.21-7.20 (m, 1H), 6.69 (d, 2H), 4.42 (d, 2H), 4.20 (s, 2H).

EXAMPLE 49

Synthesis of 2-(4-((2',4',6'-trimethylbiphenyl-3-yl) methylamino)phenylsulfonyl)acetic acid

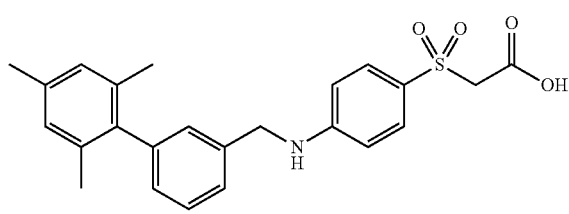 [SMILES: Cc1cc(C)c(-c2cccc(CNc3ccc(S(=O)(=O)CC(=O)O)cc3)c2)c(C)c1]

The compound was obtained in the same manner as described in Preparation Example 2.

¹H NMR (400 MHz, DMSO-d₆) δ 7.50 (d, 2H), 7.42-7.31 (m, 2H), 7.05 (s, 1H), 6.98 (d, 1H), 6.89 (s, 2H), 6.68 (d, 2H), 4.42 (d, 2H), 4.20 (s, 2H), 2.24 (s, 3H), 1.87 (s, 6H).

EXAMPLE 50

Synthesis of 2-(4-((2'-methoxybiphenyl-3-yl)methylamino)phenylsulfonyl)acetic acid

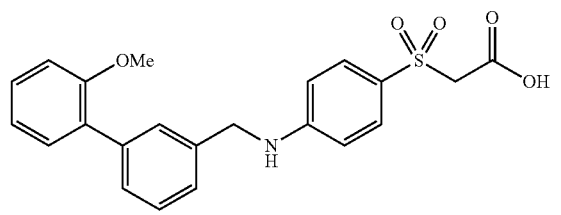 [SMILES: COc1ccccc1-c1cccc(CNc2ccc(S(=O)(=O)CC(=O)O)cc2)c1]

The compound was obtained in the same manner as described in Preparation Example 2.

¹H NMR (400 MHz, DMSO-d₆) δ 7.53 (d, 2H), 7.45-7.25 (m, 5H), 7.09 (d, 1H), 7.01 (t, 1H), 6.71 (d, 2H), 4.40 (d, 2H), 4.20 (s, 2H), 3.70 (s, 3H).

EXAMPLE 51

Synthesis of 2-(4-((4'-fluoro-2'-methylbiphenyl-3-yl)methylamino)phenylsulfonyl)acetic acid

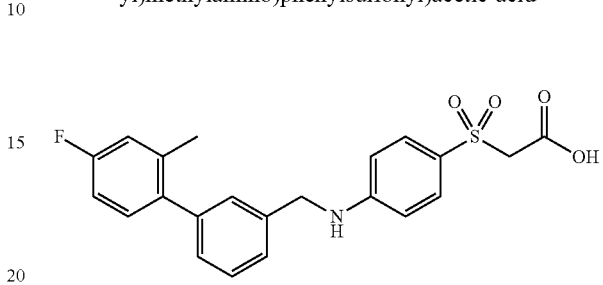

The compound was obtained in the same manner as described in Preparation Example 2.

¹H NMR (400 MHz, DMSO-d₆) δ 7.52 (d, 2H), 7.41 (t, 1H), 7.34 (d, 1H), 7.29 (s, 1H), 7.22-7.19 (m, 2H), 7.15 (dd, 1H), 7.07 (td, 1H), 6.70 (d, 2H), 4.42 (s, 2H), 4.20 (s, 2H), 2.17 (s, 3H).

EXAMPLE 52

Synthesis of 2-(4-((2'-(trifluoromethyl)biphenyl-3-yl)methylamino)phenylsulfonyl)acetic acid

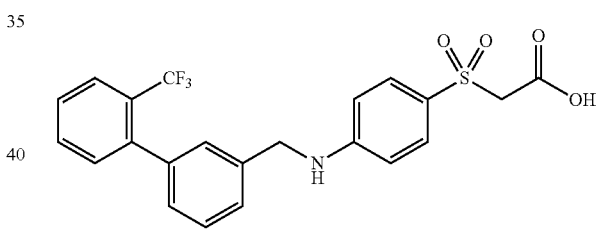

The compound was obtained in the same manner as described in Preparation Example 2.

¹H NMR (400 MHz, DMSO-d₆) δ 7.82 (d, 2H), 7.71 (t, 1H), 7.61 (t, 1H), 7.51 (d, 2H), 7.46-7.35 (d, 3H), 7.30 (s, 1H), 7.21-7.18 (m, 1H), 6.69 (d, 2H), 4.42 (s, 2H), 4.20 (s, 2H).

EXAMPLE 53

Synthesis of 2-(4-((5'-chloro-2'-methylbiphenyl-3-yl)methylamino)phenylsulfonyl)acetic acid

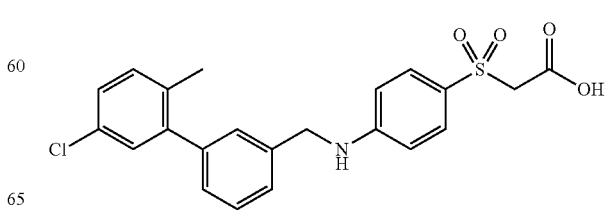

The compound was obtained in the same manner as described in Preparation Example 2.
¹H NMR (400 MHz, DMSO-d₆) δ 7.52 (d, 2H), 7.43 (t, 1H), 7.40-7.32 (d, 4H), 7.25-7.22 (m, 2H), 6.71 (d, 2H), 4.42 (d, 2H), 4.19 (s, 2H), 2.14 (s, 3H).

EXAMPLE 54

Synthesis of 2-(4-((2',6'-dimethoxybiphenyl-3-yl)methylamino)phenylsulfonyl)acetic acid

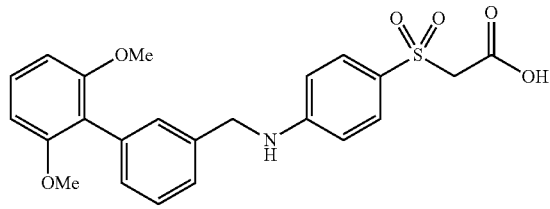 [SMILES: COc1cccc(OC)c1-c1cccc(CNc2ccc(S(=O)(=O)CC(=O)O)cc2)c1]

The compound was obtained in the same manner as described in Preparation Example 2.
¹H NMR (400 MHz, DMSO-d₆) δ 7.52 (d, 2H), 7.34-7.24 (m, 3H), 7.18 (s, 1H), 7.08 (d, 1H), 6.73-6.70 (m, 4H), 4.36 (s, 2H), 4.20 (s, 2H), 6.31 (s, 6H).

EXAMPLE 55

Synthesis of 2-(4-((2'-(hydroxymethyl)biphenyl-3-yl)methylamino)phenylsulfonyl)acetic acid

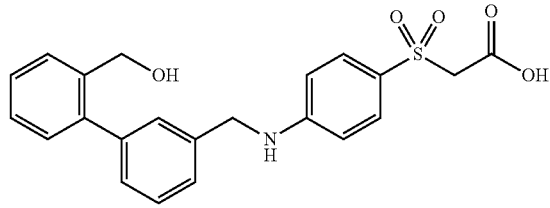 [SMILES: O=C(O)CS(=O)(=O)c1ccc(NCc2cccc(-c3ccccc3CO)c2)cc1]

The compound was obtained in the same manner as described in Preparation Example 2.
¹H NMR (400 MHz, DMSO-d₆) δ 7.57 (d, 1H), 7.53 (d, 2H), 7.42-7.269 (m, 6H), 7.19 (d, 1H), 6.72 (d, 2H), 4.41 (s, 2H), 4.38 (s, 2H), 4.20 (s, 2H).

EXAMPLE 56

Synthesis of 2-(4-((2',6-dimethylbiphenyl-3-yl)methylamino)phenylsulfonyl)acetic acid

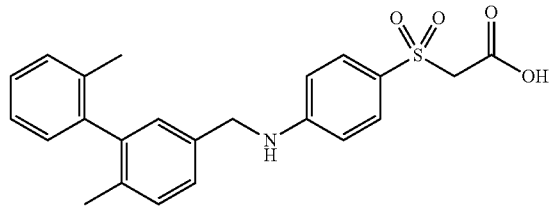 [SMILES: Cc1ccccc1-c1cc(CNc2ccc(S(=O)(=O)CC(=O)O)cc2)ccc1C]

The compound was obtained in the same manner as described in Preparation Example 2.
¹H NMR (400 MHz, DMSO-d₆) δ 7.55 (d, 2H), 7.20-7.30 (m, 6H), 7.05 (d, 2H), 6.72 (d, 2H), 4.36 (d, 2H), 4.15 (s, 2H), 1.95 (d, 3H), 1.90 (s, 3H).

EXAMPLE 57

Synthesis of 2-(4-((4-fluoro-2',6-dimethylbiphenyl-3-yl)methylamino)phenylsulfonyl)acetic acid

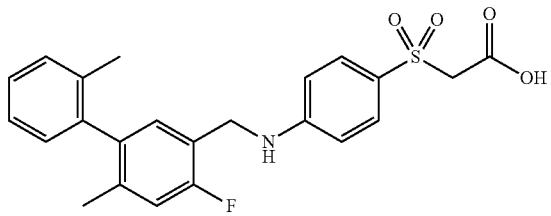 [SMILES: Cc1ccccc1-c1cc(CNc2ccc(S(=O)(=O)CC(=O)O)cc2)c(F)cc1C]

The compound was obtained in the same manner as described in Preparation Example 2.
¹H NMR (400 MHz, DMSO-d₆) δ 7.55 (d, 2H), 7.15-7.30 (m, 5H), 7.05 (d, 1H), 7.00 (d, 1H), 6.72 (d, 2H), 4.38 (d, 2H), 3.77 (s, 2H), 1.97 (s, 3H), 1.81 (s, 3H).

EXAMPLE 58

Synthesis of 2-(4-((2',6-dimethylbiphenyl-3-yl)methoxy)phenylsulfonyl)acetic acid

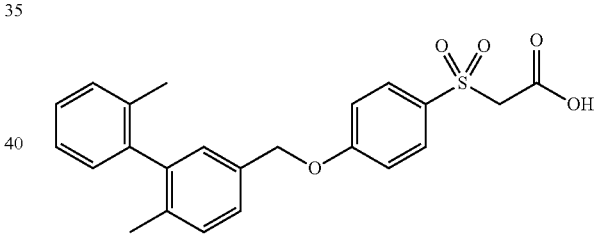

The compound was obtained in the same manner as described in Preparation Example 2.
¹H NMR (400 MHz, CDCl₃) δ 7.91 (d, 2H), 7.25-7.35 (m, 5H), 7.10-7.19 (m, 3H), 5.13 (s, 2H), 4.12 (s, 2H), 2.14 (s, 3H), 2.08 (s, 3H).

EXAMPLE 59

Synthesis of 2-(4-((2'-ethyl-6-methylbiphenyl-3-yl)methoxy)phenylsulfonyl)acetic acid

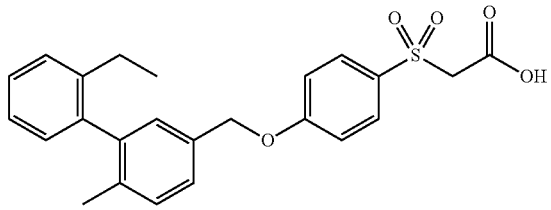 [SMILES: CCc1ccccc1-c1cc(COc2ccc(S(=O)(=O)CC(=O)O)cc2)ccc1C]

The compound was obtained in the same manner as described in Preparation Example 2.

¹H NMR (400 MHz, CDCl₃) δ 7.91 (d, 2H), 7.25-7.35 (m, 5H), 7.10-7.19 (m, 3H), 5.13 (s, 2H), 4.12 (s, 2H), 2.25-2.45 (m, 2H) 2.07 (s, 3H), 1.01 (t, 3H).

EXAMPLE 60

Synthesis of 2-(4-((2'-methylbiphenyl-3-yl)methyl-amino)phenylsulfinyl)acetic acid

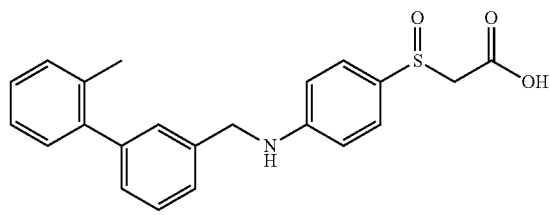 [SMILES: Cc1ccccc1-c1cccc(CNc2ccc(S(=O)CC(=O)O)cc2)c1]

The compound was obtained in the same manner as described in Preparation Example 3.

¹H NMR (400 MHz, DMSO-d₆) δ 7.20-7.42 (m, 10H), 6.97 (bs, 1H), 6.72 (d, 2H), 4.39 (s, 2H), 3.76 (s, 2H), 2.16 (s, 3H).

EXAMPLE 61

Synthesis of 2-(4-((2',6-dimethylbiphenyl-3-yl)methylamino)phenylsulfinyl)acetic acid

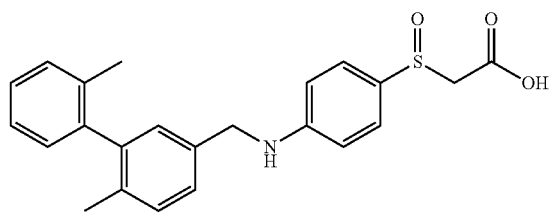 [SMILES: Cc1ccccc1-c1cc(CNc2ccc(S(=O)CC(=O)O)cc2)ccc1C]

The compound was obtained in the same manner as described in Preparation Example 3.

¹H NMR (400 MHz, DMSO-d₆) δ 7.40 (d, 2H), 7.22-7.27 (m, 5H), 7.04 (s, 1H), 6.90 (bs, 1H), 6.69 (d, 2H), 4.31 (s, 2H), 3.74 (s, 2H), 1.98 (s, 3H), 1.96 (s, 3H).

EXAMPLE 62

Synthesis of 2-(4-((4-fluoro-2',6-dimethylbiphenyl-3-yl)methylamino)phenylsulfinyl)acetic acid

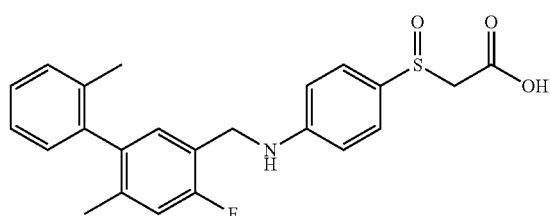

The compound was obtained in the same manner as described in Preparation Example 3.

¹H NMR (400 MHz, DMSO-d₆) δ 7.40 (d, 2H), 7.01-7.26 (m, 6H), 6.82 (bs, 1H), 6.70 (d, 2H), 4.36 (s, 2H), 3.75 (s, 2H), 1.97 (s, 3H), 1.88 (s, 3H).

EXAMPLE 63

Synthesis of 2-(4-(3-phenoxybenzylamino)phenylsulfinyl)acetic acid

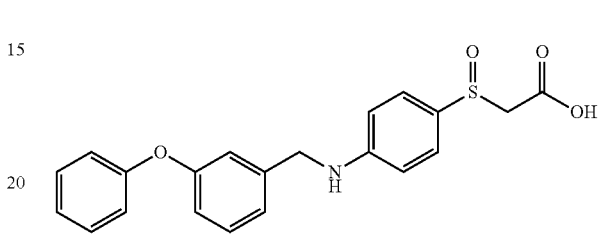

The compound was obtained in the same manner as described in Preparation Example 3.

¹H NMR (400 MHz, DMSO-d₆) δ 7.30-7.50 (m, 5H), 6.80-7.20 (m, 7H), 6.82 (bs, 1H), 6.70 (d, 2H), 4.33 (s, 2H), 3.76 (s, 2H).

EXAMPLE 64

Synthesis of 2-(4-((9,10-dihydrophenanthrene-3-yl)methylamino)phenylsulfinyl)acetic acid

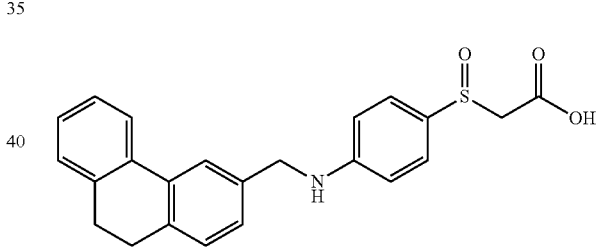

The compound was obtained in the same manner as described in Preparation Example 3.

¹H NMR (400 MHz, DMSO-d₆) δ 7.30-7.50 (m, 2H), 7.20-7.50 (m, 8H), 6.73 (d, 2H), 4.33 (s, 2H), 3.75 (s, 2H), 2.80 (m, 4H).

EXPERIMENTAL EXAMPLE 1

GPR40 Agonist Cell Assay

Meanwhile, GPR40, which is a type of G-protein coupled receptor (GPCR), is a free fatty acid (free fatty acid; FFAs) receptor abundantly expressed from the pancreas, and it has been reported that a compound acting as a GPR40 ligand is effective in treating diabetes (International Patent Application WO 2004/041266 and U.S. Pat. No. 7,960,369)

In order to confirm the regulatory activity of the compound according to the present invention on GPR40 signaling path, an assay was carried out as described below using a cell line in which human GPR40 is over-expressed in CHO cells. Specifically, the cells were cultured in a flask, and were then treated with 0.25% trypsin such that the cells could be separated from the flask surface. The trypsin reaction was ceased by adding a culture medium, and the cells were centrifuged and collected. The collected cells were suspended in a culture medium, aliquoted into each well of a 96-well black plate at 6×10$^4$ cell/100 μL, and cultured for 24 hours in an incubator. After removing the medium, the cells were treated with 100 μL of Fluo-4NW dye each according to the instruction of the Fluo-4NW calcium assay kit (F362056) and reacted for 2 hours in a cell incubator.

All compounds including the control groups were prepared at a 10 mM concentration and then subjected to a 3-fold step dilution with DMSO starting from the maximum concentration of 6 mM. The step diluted compounds were again diluted 6-fold in concentrations of 6000 nM, 2000 nM, 667 nM, 222 nM, 74 nM, 25 nM, and 8 nM in the 96-well plate using a calcium buffer solution, and were ready to be used.

After the completion of the 2-hour reaction, 20 μL of 6-fold diluted compounds were added to the cells loaded with 100 μL of Fluo-4NW dye, and fluorescence was measured at 4 second intervals for 120 seconds using Synergy Neo (Bio-Teck). Each compound was treated with the final concentrations of 1000 nM, 333 nM, 111 nM, 37 nM, 12 nM, 4 nM, and 1 nM. The results were measured by correcting the default values before the treatment of test materials with RFU values obtained during the measurement, and a dose-response graph was obtained by taking the maximum RFU values for each concentration, and an EC$_{50}$ value, which refers to the concentration showing 50% activity of the maximum value, was calculated.

As a result, the compound of the present invention showed an excellent activity with the EC$_{50}$ value of 100 nM or less.

EXPERIMENTAL EXAMPLE 2

Oral Glucose Tolerance Test (OGTT) in ICR Mice

In order to evaluate the ability to control blood glucose in the body for the compound according to the present invention, an oral glucose tolerance test was conducted using ICR mice. The day before the test, normal ICR mice were separated into four per group, and were fasted for at least 16 hours. The body weight of each mouse was measured and recorded in the morning on the day of the test; The compound was prepared in a concentration of 5 mg/mL in 0.5% methylcellulose such that it could be administered at a dose of 50 mg/kg, and was then further diluted to be in concentrations of 2 mg/kg, 0.5 mg/kg, and 0.1 mg/kg and administered at the same volume such that it can be administered at doses of 20 mg/kg, 5 mg/kg, and 1 mg/kg. Glucose was dissolved in drinking water and prepared in a concentration of 200 mg/mL such that it could be administered at a dose of 2 g/kg. Before administering the compounds, a small amount of blood of the mice was drawn from the caudal vein, and blood glucose was measured using ACCU-CHEK Active (Art. No. 2248891001), a blood glucose meter, and recorded. A solvent (0.5% MC) as a vehicle and the compounds prepared above were administered to all mice at a dose of 10 mL per 1 kg of body weight using a sonde. Glucose was further administered, and the blood glucose was measured in each mouse after 0.5 hours, 1 hour, and 2 hours.

The obtained results are shown as the means and standard deviations of blood glucose according to each experimental group and measurement time, and glucose AUCO-2 hr values were calculated for 2 hours after glucose administration from the amount of change of blood glucose over time using the WinNonlin Professional (ver 5.3) program. Based on the calculated individual AUCO-2 hr value, a significant effect of lowering blood glucose was confirmed statistically by analyzing each group via student's t-test analysis (p<0.05). Representatively, the results measured for the compound of Example 1 are shown in the drawing.

What is claimed is:
1. A compound represented by Formula 1 below or a pharmaceutically acceptable salt thereof:

[Formula 1]

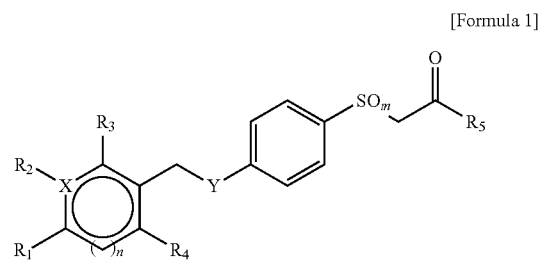

wherein
X is C or O;
Y is NH or O;
m is an integer of 1 or 2;
n is an integer of 0 or 1;
R$_1$ is hydrogen, C$_{1-4}$ alkyl, or C$_{1-4}$ alkoxy; or forms a C$_{5-10}$ hydrocarbon ring connected with R$_2$;
R$_2$ is absent or hydrogen, halogen, aryloxy, or aryl or heteroaryl selected from the group consisting of phenyl, pyrazinyl, pyrazolyl, pyridinyl, pyrimidinyl, thiazolyl, and thienyl,
wherein the aryl or heteroaryl is unsubstituted, or independently substituted with at least one substituent selected from the group consisting of C$_{1-4}$ alkyl, C$_{1-4}$ alkoxy, haloalkyl, C$_{1-4}$ hydroxyalkyl, hydroxy, halogen, nitro, cyano, amino, C$_{1-4}$ alkyl-amino, acetyl-amino, formyl, —(C═O)—(C$_{1-4}$ alkyl), —(C═O)-morpholino, —(C═O)—NR$_6$R$_7$, morpholino, piperazinyl, piperidinyl, C$_{1-4}$ alkyl-SO$_2$—C$_{1-4}$ alkoxy, —SO$_2$—(C$_{1-4}$ alkyl), and —SO$_2$—NR$_6$R$_7$ directly or through a straight or branched C$_{1-4}$ alkyl chain, or forms an unsubstituted or halogen substituted 5- to 7-membered ring joined through two adjacent substituent groups, said ring comprising 0 to 2 oxygen atoms;
R$_3$ and R$_4$ are each independently hydrogen, halogen, C$_{1-4}$ alkyl, C$_{1-4}$ alkoxy, nitro, cyano, amino, C$_{1-4}$ alkyl-amino, acetyl-amino, formyl, —(C═O)—(C$_{1-4}$ alkyl), —(C═O)-morpholino, —(C═O)—NR$_6$R$_7$, morpholino, piperazinyl, piperidinyl, —SO$_2$—(C$_{1-4}$ alkyl), or —SO$_2$—NR$_6$R$_7$;
R$_5$ is hydroxy, C$_{1-4}$ alkoxy, or C$_{1-4}$ alkyl-aminooxy; and
R$_6$ and R$_7$ are each independently hydrogen or C$_{1-4}$ alkyl,
wherein
when X is O, then n is 0 and R$_2$ is absent; and
when X is C, then n is 1, and provided further that when R$_2$ is hydrogen, then R$_1$ is C$_{1-4}$ alkyl or C$_{1-4}$ alkoxy, or R$_3$ is halogen, C$_{1-4}$ alkyl, C$_{1-4}$ alkoxy, nitro, cyano, amino, C$_{1-4}$ alkyl-amino, acetyl-amino, formyl, —(C═O)—(C$_{1-4}$ alkyl), —(C═O)-morpholino, —(C═O) —NR$_6$R$_7$, morpholino, piperazinyl, piperidinyl, —SO$_2$—(C$_{1-4}$ alkyl), or —SO$_2$—NR$_6$R$_7$.

2. The compound or pharmaceutically acceptable salt thereof of claim 1, wherein $R_1$ is hydrogen, methyl, or ethoxy, or forms a $C_{5-10}$ hydrocarbon ring connected with $R_2$.

3. The compound or pharmaceutically acceptable salt thereof of claim 1,
wherein $R_2$ is absent; $R_2$ is hydrogen; halogen; aryloxy; or $R_2$ is phenyl or pyridinyl which is unsubstituted or independently substituted with 1 to 3 substituents selected from the group consisting of $C_{1-4}$ alkyl, $C_{1-4}$ alkoxy, $C_{1-4}$ haloalkyl, $C_{1-4}$ hydroxyalkyl, $C_{1-4}$ alkyl-$SO_2$—$C_{1-4}$ alkoxy, hydroxy, and halogen, or forms an unsubstituted or halogen-substituted 5- to 7-membered ring joined through two adjacent substituent groups, said ring comprising 0 to 2 oxygen atoms.

4. The compound or pharmaceutically acceptable salt thereof of claim 3, wherein $R_2$ is absent; $R_2$ is hydrogen; bromo; phenyloxy; benzofuranyl; 2,3-dihydrobenzo[b][1,4]dioxynyl; or $R_2$ is phenyl, pyridinyl, or benzo[d][1,3]dioxolyl unsubstituted or substituted with 1 to 3 substituents selected from the group consisting of methyl, ethyl, methoxy, ethoxy, trifluoromethyl, hydroxymethyl, methylsulfonyl-propoxy, hydroxy, fluoro, and chloro.

5. The compound or pharmaceutically acceptable salt thereof of claim 1, wherein $R_3$ and $R_4$ are each independently hydrogen, halogen, $C_{1-4}$ alkyl, $C_{1-4}$ alkoxy, nitro, cyano, or amino.

6. The compound or pharmaceutically acceptable salt thereof of claim 5, wherein $R_3$ and $R_4$ are each independently hydrogen, fluoro, methyl, or methoxy.

7. The compound or pharmaceutically acceptable salt thereof of claim 1, wherein $R_5$ is hydroxy.

8. The compound or pharmaceutically acceptable salt thereof of claim 1, wherein
when X is C,
Y is NH or O;
m is an integer of 1 or 2;
n is an integer of 1;
$R_1$ is hydrogen, methyl, or ethoxy, or forms a tetrahydronaphthalene ring connected with $R_2$;
$R_2$ is hydrogen; bromo; phenyloxy; benzofuranyl; 2,3-dihydrobenzo[b][1,4]dioxynyl; or phenyl, pyridinyl, or benzo[d][1,3]dioxolyl unsubstituted or substituted with 1 to 3 substituents selected from the group consisting of methyl, ethyl, methoxy, ethoxy, trifluoromethyl, hydroxymethyl, methyl-sulfonyl-propoxy, hydroxy, fluoro, and chloro;
$R_3$ and $R_4$ are each independently hydrogen, fluoro, methyl, or methoxy; and
$R_5$ is hydroxy.

9. The compound or pharmaceutically acceptable salt thereof of claim 1, wherein
when X is O,
Y is NH;
m is an integer of 1 or 2;
n is an integer of 0;
$R_1$ is hydrogen;
$R_2$ is absent;
$R_3$ and $R_4$ are both hydrogen; and
$R_5$ is hydroxy.

10. The compound or pharmaceutically acceptable salt thereof of claim 1, wherein the compound is selected from the group consisting of:
1) 2-(4-((2'-methyl-biphenyl-3-yl)methylamino)phenylsulfonyl)acetic acid,
2) 2-(4-(3-(benzofuran-5-yl)benzylamino)phenylsulfonyl)acetic acid,
3) 2-(4-(3-phenoxybenzylamino)phenylsulfonyl)acetic acid,
4) 2-(4-(3-bromobenzylamino)phenylsulfonyl)acetic acid,
5) 2-(4-((2',6'-dimethyl-4'-(3-(methylsulfonyl)propoxy)biphenyl-3-yl)methylamino)phenylsulfonyl)acetic acid,
6) 2-(4-((2',6'-dimethylbiphenyl-3-yl)methylamino)phenylsulfonyl)acetic acid,
7) 2-(4-((4'-fluorobiphenyl-3-yl)methylamino)phenylsulfonyl)acetic acid,
8) 2-(4-((3'-methoxybiphenyl-3-yl)methylamino)phenylsulfonyl)acetic acid,
9) 2-(4-((4-fluoro-2'-methylbiphenyl-3-yl)methylamino)phenylsulfonyl)acetic acid,
10) 2-(4-((2',4-dimethylbiphenyl-3-yl)methylamino)phenylsulfonyl)acetic acid,
11) 2-(4-((4-methoxy-2'-methylbiphenyl-3-yl)methylamino)phenylsulfonyl)acetic acid,
12) 2-(4-((2-fluoro-2'-methylbiphenyl-3-yl)methylamino)phenylsulfonyl)acetic acid,
13) 2-(4-((2-methoxy-2'-methylbiphenyl-3-yl)methylamino)phenylsulfonyl)acetic acid,
14) 2-(4-((4-fluoro-2',3'-dimethylbiphenyl-3-yl)methylamino)phenylsulfonyl)acetic acid,
15) 2-(4-((4-fluoro-2',4'-dimethylbiphenyl-3-yl)methylamino)phenylsulfonyl)acetic acid,
16) 2-(4-((2-fluorobiphenyl-3-yl)methylamino)phenylsulfonyl)acetic acid,
17) 2-(4-((2-methoxybiphenyl-3-yl)methylamino)phenylsulfonyl)acetic acid,
18) 2-(4-((4-methoxy-2',3'-dimethylbiphenyl-3-yl)methylamino)phenylsulfonyl)acetic acid,
19) 2-(4-(2-methoxybenzylamino)phenylsulfonyl)acetic acid,
20) 2-(4-(3-methoxybenzylamino)phenylsulfonyl)acetic acid,
21) 2-(4-(2-methylbenzylamino)phenylsulfonyl)acetic acid,
22) 2-(4-(4-ethoxybenzylamino)phenylsulfonyl)acetic acid,
23) 2-(4-(furan-3-yl-methylamino)phenylsulfonyl)acetic acid,
24) 2-(4-(3-(pyridin-3-yl)benzylamino)phenylsulfonyl)acetic acid,
25) 2-(4-(3-(pyridin-4-yl)benzylamino)phenylsulfonyl)acetic acid,
26) 2-(4-(3-(benzo[d][1,3]dioxol-5-yl)benzylamino)phenylsulfonyl)acetic acid,
27) 2-(4-(3-(2,2-difluoro-benzo[d][1,3]dioxol-5-yl)benzylamino)phenylsulfonyl)acetic acid,
28) 2-(4-(3-(4-fluoro-benzo[d][1,3]dioxol-5-yl)benzylamino)phenylsulfonyliacetic acid,
29) 2-(4-(3-(2,3-dihydrobenzo[b][1,4]dioxin-6-yl)benzylamino)phenylsulfonyl)acetic acid,
30) 2-(4-(3-(2-methylpyridin-4-yl)benzylamino)phenylsulfonyl)acetic acid,
31) 2-(4-(3 -(2-hydroxypyridin-4-yl)benzylamino)phenylsulfonyl)acetic acid,
32) 2-(4-(3 -(2-methoxypyridin-4-yl)benzylamino)phenylsulfonyl)acetic acid,
33) 2-(4-(3 -(2-ethoxypyridin-4-yl)benzylamino)phenylsulfonyl)acetic acid,
34) 2-(4-((4'-methylbiphenyl-3-yl)methylamino)phenylsulfonyl)acetic acid,
35) 2-(4-(biphenyl-3-yl-methylamino)phenylsulfonyl)acetic acid, 36) 2-(4-((3',4'-dimethylbiphenyl-3-yl)methylamino)phenylsulfonyl)acetic acid,
37) 2-(4-((2',4'-dimethylbiphenyl-3-yl)methylamino)phenylsulfonyl)acetic acid,
38) 2-(4-((2',3'-dimethylbiphenyl-3-yl)methylamino)phenylsulfonyl)acetic acid,
39) 2-(4-((2',5'-dimethylbiphenyl-3-yl)methylamino)phenylsulfonyl)acetic acid,
40) 2-(4-((4'-ethylbiphenyl-3-yl-methylamino)phenylsulfonyl)acetic acid,
41) 2-(4-((2'-ethylbiphenyl-3-yl)methylamino)phenylsulfonyl)acetic acid,
42) 2-(4-((3',5'-dimethylbiphenyl-3-yl)methylamino)phenylsulfonyl)acetic acid,
43) 2-(4-((4'-methoxy-2'-methylbiphenyl-3-yl)methylamino)phenylsulfonyl)acetic acid,
44) 2-(4-((4'-methoxy-2',6'-dimethylbiphenyl-3-yl)methylamino)phenylsulfonyl)acetic acid,
45) 2-(4-((3'-methylbiphenyl-3-yl)methylamino)phenylsulfonyl)acetic acid,
46) 2-(4-((3',4'-dimethoxybiphenyl-3-yl)methylamino)phenylsulfonyl)acetic acid,
47) 2-(4-((4'-chloro-2'-methylbiphenyl-3-yl)methylamino)phenylsulfonyl)acetic acid,
48) 2-(4-((4'-chloro-2'-(trifluoromethyl)biphenyl-3-yl)methylamino)phenylsulfonyl)acetic acid,
49) 2-(4-((2',4',6'-trimethylbiphenyl-3-yl)methylamino)phenylsulfonyl)acetic acid,
50) 2-(4-((2'-methoxybiphenyl-3-yl)methylamino)phenylsulfonyl)acetic acid,
51) 2-(4-((4'-fluoro-2'-methylbiphenyl-3-yl)methylamino)phenylsulfonyl)acetic acid,
52) 2-(4-((2'-(trifluoromethyl)biphenyl-3-yl)methylamino)phenylsulfonyl)acetic acid,
53) 2-(4-((5'-chloro-2'-methylbiphenyl-3-yl)methylamino)phenylsulfonyl)acetic acid,
54) 2-(4-((2',6'-dimethoxybiphenyl-3-yl)methylamino)phenylsulfonyl)acetic acid,
55) 2-(4-((2'-(hydroxymethyl)biphenyl-3-yl)methylamino)phenylsulfonyl)acetic acid,
56) 2-(4-((2',6-dimethylbiphenyl-3-yl)methylamino)phenylsulfonyl)acetic acid,
57) 2-(4-((4-fluoro-2',6'-dimethylbiphenyl-3-yl)methylamino)phenylsulfonyl)acetic acid,
58) 2-(4-((2',6'-dimethylbiphenyl-3-yl)methoxy)phenylsulfonyl)acetic acid,
59) 2-(4-((2'-ethyl-6-methylbiphenyl-3-yl)methoxy)phenylsulfonyl)acetic acid,
60) 2-(4-((2'-methylbiphenyl-3-yl)methylamino)phenylsulfinyl)acetic acid,
61) 2-(4-((2',6-dimethylbiphenyl-3-yl)methylamino)phenylsulfinyl)acetic acid,
62) 2-(4-((4-fluoro-2',6'-dimethylbiphenyl-3-yl)methylamino)phenylsulfinyl)acetic acid,
63) 2-(4-(3-phenoxybenzylamino)phenylsulfinyl)acetic acid, and
64) 2-(4-((9,10-dihydrophenanthrene-3-yl)methylamino)phenylsulfinyl)acetic acid.

11. The compound or pharmaceutically acceptable salt thereof of claim 1,
wherein
X is C;
Y is NH or O;
m is an integer of 1 or 2;
n is an integer of 1;
$R_1$ is hydrogen, $C_{1-4}$ alkyl, or $C_{1-4}$ alkoxy; or forms a $C_{5-10}$ hydrocarbon ring connected with $R_2$;

$R_2$ is halogen, aryloxy, or aryl or heteroaryl selected from the group consisting of phenyl, pyrazinyl, pyrazolyl, pyridinyl, pyrimidinyl, thiazolyl, and thienyl,
wherein the aryl or heteroaryl is unsubstituted, or independently substituted with at least one substituent selected from the group consisting of $C_{1-4}$ alkyl, $C_{1-4}$ alkoxy, $C_{1-4}$ haloalkyl, $C_{1-4}$ hydroxyalkyl, hydroxy, halogen, nitro, cyano, amino, $C_{1-4}$ alkyl-amino, acetyl-amino, formyl, —(C=O)—($C_{1-4}$ alkyl), —(C=O)-morpholino, —(C=O)—$NR_6R_7$, morpholino, piperazinyl, piperidinyl, $C_{1-4}$ alkyl-$SO_2$—$C_{1-4}$ alkoxy, —$SO_2$—($C_{1-4}$ alkyl), and —$SO_2$—$NR_6R_7$ directly or through a straight or branched $C_{1-4}$ alkyl chain, or forms an unsubstituted or halogen substituted 5- to 7-membered ring joined through two adjacent substituent groups, said ring comprising 0 to 2 oxygen atoms;
$R_3$ and $R_4$ are each independently hydrogen, halogen, $C_{1-4}$ alkyl, $C_{1-4}$ alkoxy, nitro, cyano, amino, $C_{1-4}$ alkyl-amino, acetyl-amino, formyl, —(C=O)—($C_{1-4}$ alkyl), —(C=O)-morpholino, —(C=O)-$NR_6R_7$, morpholino, piperazinyl, piperidinyl, —$SO_2$—($C_{1-4}$ alkyl), or —$SO_2$—$NR_6R_7$;
$R_5$ is hydroxy, $C_{1-4}$ alkoxy, or $C_{1-4}$ alkyl-aminooxy; and
$R_6$ and $R_7$ are each independently hydrogen or $C_{1-4}$ alkyl;
or
X is O;
Y is NH or O;
m is an integer of 1 or 2;
n is the integer of 0;
$R_1$ is hydrogen, $C_{1-4}$ alkyl, or $C_{1-4}$ alkoxy; or forms a $C_{5-10}$ hydrocarbon ring connected with $R_2$;
$R_2$ is absent;
$R_3$ and $R_4$ are each independently hydrogen, halogen, $C_{1-4}$ alkyl, $C_{1-4}$ alkoxy, nitro, cyano, amino, $C_{1-4}$ alkyl-amino, acetyl-amino, formyl, —(C=O)—($C_{1-4}$ alkyl), —(C=O)-morpholino, —(C=O)—$NR_6R_7$, morpholino, piperazinyl, piperidinyl, —$SO_2$—($C_{1-4}$ alkyl), or —$SO_2$—$NR_6R_7$;
$R_5$ is hydroxy, $C_{1-4}$ alkoxy, or $C_{1-4}$ alkyl-aminooxy; and
$R_6$ and $R_7$ are each independently hydrogen or $C_{1-4}$ alkyl.

12. A pharmaceutical composition for
treating diabetes comprising the compound or pharmaceutically acceptable salt thereof according to claim 1 as an active ingredient.

13. The pharmaceutical composition of claim 12, wherein the compound or a pharmaceutically acceptable salt thereof enhances glucose metabolism.

14. The pharmaceutical composition of claim 12, wherein $R_1$ is hydrogen, methyl, or ethoxy, or forms a $C_{5-10}$ hydrocarbon ring connected with $R_2$.

15. The pharmaceutical composition of claim 12,
wherein $R_2$ is absent; $R_2$ is hydrogen; halogen; aryloxy; or $R_2$ is phenyl or pyridinyl which is unsubstituted or independently substituted with 1 to 3 substituents selected from the group consisting of $C_{1-4}$ alkyl, $C_{1-4}$ alkoxy, $C_{1-4}$ haloalkyl, $C_{1-4}$ hydroxyalkyl, $C_{1-4}$ alkyl-$SO_2$—$C_{1-4}$ alkoxy, hydroxy, and halogen, or forms an unsubstituted or halogen-substituted 5- to 7-membered ring joined through two adjacent substituent groups, said ring comprising 0 to 2 oxygen atoms.

16. The pharmaceutical composition of claim 15,
wherein $R_2$ is absent; $R_2$ is hydrogen; bromo; phenyloxy; benzofuranyl; 2,3-dihydrobenzo[b][1,4]dioxynyl; or $R_2$ is phenyl, pyridinyl, or benzo[d][1,3]dioxolyl unsubstituted or substituted with 1 to 3 substituents selected from the group consisting of methyl, ethyl, methoxy, ethoxy, trifluoromethyl, hydroxymethyl, methyl-sulfonyl-propoxy, hydroxy, fluoro, and chloro.

17. The pharmaceutical composition of claim 12, wherein $R_3$ and $R_4$ are each independently hydrogen, halogen, $C_{1-4}$ alkyl, $C_{1-4}$ alkoxy, nitro, cyano, or amino.

18. The pharmaceutical composition of claim 17, wherein $R_3$ and $R_4$ are each independently hydrogen, fluoro, methyl, or methoxy.

19. The pharmaceutical composition of claim 12, wherein $R_5$ is hydroxy.

20. The pharmaceutical composition of claim 12, wherein when X is C,
Y is NH or O;
m is an integer of 1 or 2;
n is an integer of 1;
$R_1$ is hydrogen, methyl, or ethoxy, or forms a tetrahydronaphthalene ring connected with $R_2$;
$R_2$ is hydrogen; bromo; phenyloxy; benzofuranyl; 2,3-dihydrobenzo[b][1,4]dioxynyl; or phenyl, pyridinyl, or benzo[d][1,3]dioxolyl unsubstituted or substituted with 1 to 3 substituents selected from the group consisting of methyl, ethyl, methoxy, ethoxy, trifluoromethyl, hydroxymethyl, methyl-sulfonyl-propoxy, hydroxy, fluoro, and chloro;
$R_3$ and $R_4$ are each independently hydrogen, fluoro, methyl, or methoxy; and
$R_5$ is hydroxy.

21. The pharmaceutical composition of claim 12, wherein when X is O,
Y is NH;
m is an integer of 1 or 2;
n is an integer of 0;
$R_1$ is hydrogen;
$R_2$ is absent;
$R_3$ and $R_4$ are both hydrogen; and
$R_5$ is hydroxy.

22. The pharmaceutical composition of claim 12, wherein the compound is selected from the group consisting of:
1) 2-(4-((2'-methyl-biphenyl-3-yl)methylamino)phenylsulfonyl)acetic acid,
2) 2-(4-(3-(benzofuran-5-yl)benzylamino)phenylsulfonyl)acetic acid,
3) 2-(4-(3-phenoxybenzylamino)phenylsulfonyl)acetic acid,
4) 2-(4-(3-bromobenzylamino)phenylsulfonyl)acetic acid,
5) 2-(4-((2',6'-dimethyl-4'-(3-(methylsulfonyl)propoxy)biphenyl-3-yl)methylamino)phenylsulfonyl)acetic acid,
6) 2-(4-((2',6'-dimethylbiphenyl-3-yl)methylamino)phenylsulfonyl)acetic acid,
7) 2-(4-((4'-fluorobiphenyl-3-yl)methylamino)phenylsulfonyl)acetic acid,
8) 2-(4-((3'-methoxybiphenyl-3-yl)methylamino)phenylsulfonyl)acetic acid,
9) 2-(4-((4-fluoro-2'-methylbiphenyl-3-yl)methylamino)phenylsulfonyl)acetic acid,
10) 2-(4-((2',4-dimethylbiphenyl-3-yl)methylamino)phenylsulfonyl)acetic acid,
11) 2-(4-((4-methoxy-2'-methylbiphenyl-3-yl)methylamino)phenylsulfonyl)acetic acid,
12) 2-(4-((2-fluoro-2'-methylbiphenyl--yl)methylamino)phenylsulfonyl)acetic acid,
13) 2-(4-((2-methoxy-2'-methylbiphenyl-3-yl)methylamino)phenylsulfonyl)acetic acid,
14) 2-(4-((4-fluoro-2',3'-dimethylbiphenyl-3-yl)methylamino)phenylsulfonyl)acetic acid,
15) 2-(4-((4-fluoro-2',4'-dimethylbiphenyl-3-yl)methylamino)phenylsulfonyl)acetic acid,
16) 2-(4-((2-fluorobiphenyl-3-yl)methylamino)phenylsulfonyl)acetic acid,
17) 2-(4-((2-methoxybiphenyl-3-yl)methylamino)phenylsulfonyl)acetic acid,
18) 2-(4-((4-methoxy-2',3'-dimethylbiphenyl-3-yl)methylamino)phenylsulfonyl)acetic acid,
19) 2-(4-(2-methoxybenzylamino)phenylsulfonyl)acetic acid,
20) 2-(4-(3-methoxybenzylamino)phenylsulfonyl)acetic acid,
21) 2-(4-(2-methylbenzylamino)phenylsulfonyl)acetic acid,
22) 2-(4-(4-ethoxybenzylamino)phenylsulfonyl)acetic acid,
23) 2-(4-(furan-3-yl-methylamino)phenylsulfonyl)acetic acid,
24) 2-(4-(3-(pyridin-3-yl)benzylamino)phenylsulfonyl)acetic acid,
25) 2-(4-(3-(pyridin-4-yl)benzylamino)phenylsulfonyl)acetic acid,
26) 2-(4-(3-(benzo[d][1,3]dioxol-5-yl)benzylamino)phenylsulfonyl)acetic acid,
27) 2-(4-(3-(4-fluoro-benzo[d][1,3]dioxol-5-yl)benzylamino)phenylsulfonyl)acetic acid,
28) 2-(4-(3-(4-fluoro-benzo[d][1,3]dioxol-5-yl)benzylamino)phenylsulfonyl)acetic acid,
29) 2-(4-(3-(2,3-dihydrobenzo[b][1,4]dioxin-6-yl)benzylamino)phenylsulfonyl)acetic acid,
30) 2-(4-(3 -(2-methylpyridin-4-yl)benzylamino)phenylsulfonyl)acetic acid,
31) 2-(4-(3 -(2-hydroxypyridin-4-yl)benzylamino)phenylsulfonyl)acetic acid,
32) 2-(4-(3 -(2-methoxypyridin-4-yl)benzylamino)phenylsulfonyl)acetic acid,
33) 2-(4-(3 -(2-ethoxypyridin-4-yl)benzylamino)phenylsulfonyl)acetic acid,
34) 2-(4-((4'-methylbiphenyl-3-yl)methylamino)phenylsulfonyl)acetic acid,
35) 2-(4-(biphenyl-3-yl-methylamino)phenylsulfonyl)acetic acid,
36) 2-(4-((3',4'-dimethylbiphenyl-3-yl)methylamino)phenylsulfonyl)acetic acid,
37) 2-(4-((2',4'-dimethylbiphenyl-3-yl)methylamino)phenylsulfonyl)acetic acid,
38) 2-(4-((2',3'-dimethylbiphenyl-3-yl)methylamino)phenylsulfonyl)acetic acid,
39) 2-(4-((2',5'-dimethylbiphenyl-3-yl)methylamino)phenylsulfonyl)acetic acid,
40) 2-(4-((4'-ethylbiphenyl-3-yl-methylamino)phenylsulfonyl)acetic acid,
41) 2-(4-((2'-ethylbiphenyl-3-yl)methylamino)phenylsulfonyl)acetic acid,
42) 2-(4-((3',5'-dimethylbiphenyl-3-yl)methylamino)phenylsulfonyl)acetic acid,
43) 2-(4-((4'-methoxy-2'-methylbiphenyl-3-yl)methylamino)phenylsulfonyl)acetic acid,
44) 2-(4-((4'-methoxy-2',6'-dimethylbiphenyl-3-yl)methylamino)phenylsulfonyl)acetic acid,
45) 2-(4-((3'-methylbiphenyl-3-yl)methylamino)phenylsulfonyl)acetic acid,
46) 2-(4-((3',4'-dimethoxybiphenyl-3-yl)methylamino)phenylsulfonyl)acetic acid,
47) 2-(4-((4'-chloro-2'-methylbiphenyl-3-yl)methylamino)phenylsulfonyl)acetic acid, 48) 2-(4-((4'-chloro-2'-(trifluoromethyl)biphenyl3-yl)methylamino)phenylsulfonyflacetic acid,
49) 2-(4-((2',4',6'-trimethylbiphenyl-3-yl)methylamino)phenylsulfonyl)acetic acid,
50) 2-(4-((2'-methoxybiphenyl-3-yl)methylamino)phenylsulfonyl)acetic acid,
51) 2-(4-((4'-fluoro-2'-methylbiphenyl-3-yl)methylamino)phenylsulfonyl)acetic acid,
52) 2-(4-((2'-(trifluoromethyl)biphenyl-3-yl)methylamino)phenylsulfonyl)acetic acid,
53) 2-(4-((5'-chloro-2'-methylbiphenyl-3-yl)methylamino)phenylsulfonyl)acetic acid,
54) 2-(4-((2',6'-dimethoxybiphenyl-3-yl)methylamino)phenylsulfonyl)acetic acid,
55) 2-(4-((2'-(hydroxymethyl)biphenyl-3-yl)methylamino)phenylsulfonyl)acetic acid,
56) 2-(4-((2',6'-dimethylbiphenyl-3-yl)methylamino)phenylsulfonyl)acetic acid,
57) 2-(4-((4-fluoro-2',6-dimethylbiphenyl-3-yl)methylamino)phenylsulfonyl)acetic acid,
58) 2-(4-((2',6-dimethylbiphenyl-3-yl)methoxy)phenylsulfonyl)acetic acid,
59) 2-(4-((2'-ethyl-6-methylbiphenyl-3-yl)methoxy)phenylsulfonyl)acetic acid,
60) 2-(4-((2'-methylbiphenyl-3-yl)methylamino)phenylsulfinyl)acetic acid,
61) 2-(4-((2',6-dimethylbiphenyl-3-yl)methylamino)phenylsulfinyl)acetic acid,
62) 2-(4-((4-fluoro-2',6-dimethylbiphenyl-3-yl)methylamino)phenylsulfinyl)acetic acid,
63) 2-(4-(3-phenoxybenzylamino)phenylsulfinyl)acetic acid, and
64) 2-(4-((9,10-dihydrophenanthrene-3-yl)methylamino)phenylsulfinyl)acetic acid.

* * * * *